United States Patent
von Recum

(10) Patent No.: US 9,642,920 B2
(45) Date of Patent: *May 9, 2017

(54) THERAPEUTIC AGENT DELIVERY SYSTEM AND METHOD

(71) Applicant: Case Western Reserve University, Cleveland, OH (US)

(72) Inventor: Horst A. von Recum, Cleveland Hts., OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/451,527

(22) Filed: Aug. 5, 2014

(65) Prior Publication Data

US 2015/0010608 A1  Jan. 8, 2015

Related U.S. Application Data

(63) Continuation-in-part of application No. 13/376,298, filed as application No. PCT/US2010/037183 on Jun. 3, 2010.

(60) Provisional application No. 61/183,698, filed on Jun. 3, 2009.

(51) Int. Cl.
| | |
|---|---|
| A61K 47/48 | (2006.01) |
| A61L 31/16 | (2006.01) |
| A61L 31/10 | (2006.01) |
| A61K 31/704 | (2006.01) |
| C08B 37/16 | (2006.01) |
| C08L 5/16 | (2006.01) |
| A61K 9/00 | (2006.01) |
| A61K 47/36 | (2006.01) |
| A61K 47/40 | (2006.01) |

(52) U.S. Cl.
CPC ...... *A61K 47/48969* (2013.01); *A61K 9/0024* (2013.01); *A61K 31/704* (2013.01); *A61K 47/36* (2013.01); *A61K 47/40* (2013.01); *C08B 37/0015* (2013.01); *C08L 5/16* (2013.01)

(58) Field of Classification Search
None
See application file for complete search history.

(56) References Cited

U.S. PATENT DOCUMENTS

| | | |
|---|---|---|
| 2005/0276841 A1 | 12/2005 | Davis et al. |
| 2006/0177483 A1* | 8/2006 | Byrne ............... A61K 9/0051 424/427 |
| 2007/0026069 A1 | 2/2007 | Shastri et al. |
| 2008/0206146 A1 | 8/2008 | Akhtari et al. |
| 2008/0254094 A1 | 10/2008 | Martel et al. |
| 2009/0176737 A1* | 7/2009 | Tabuchi ............... A61K 31/135 514/58 |
| 2012/0220518 A1 | 8/2012 | von Recum et al. |

FOREIGN PATENT DOCUMENTS

| | | | |
|---|---|---|---|
| CH | WO2003105867 A1 * | 12/2003 | ............ A61K 31/724 |
| JP | WO2007077783 A1 * | 7/2007 | ............ A61K 32/135 |

OTHER PUBLICATIONS

Kim et al. Resorbable polymer microchips releasing BCNU inhibit tumor growth in the rat 9L flank model. J Control Release. Nov. 6, 2007;123(2):172-8.*
Hoare et al. Hydrogels in drug delivery: Progress and challenges. Polymer 49 (2008) 1993-2007.*
Harada et al. Complex formation between poly(ethylene glycol) and α-cyclodextrin. Macromolecules, 1990, 23 (10), pp. 2821-2823.*
Bibby et al., Mechanisms by which cyclodextrins modify drug release from polymeric drug delivery systems, International Journal of Pharmaceutics 197: 1-11 (2000).
Cheng et al., Synthesis of linear, 13-cyclodextrin-based polymers and their camptothecin conjugates, Bioconjugate Chem. 14:1007-1017 (2003).
Van De Manakker et al., Cyclodextrin-based polymeric materials: synthesis, properties, and pharmaceutical/biomedical applications, Biomacromolecules 10(12): 3157-3175.
Fenyvesi , Cyclodextrin Polymers in the Pharmaceuticals Industry, Journal of Inclusion Phenomena, 6: 537-545 (1988).
Fenyvesi et al., Controlled Release of Drugs from CD Polymers Substituted with Ionic Groups, Journal of Inclusion Phenomena and Molecular Recognition in Chemistry, 25: 185-189 (1996).
Jenkins et al., Glossary of Basic Terms in Polymer Science, Pure & Appl. Chem, 86(12): 2287-2311 (1996).
Pun et al., Cyclodextrin-Modified Polyethylenimine Polymers for Gene Delivery, Bioconjugate Chem., 381-840 (2004).
Suh et al., A Novel Host Containing Both Binding Site and Nucleophile Prepared by Attachment of 13-Cyclodextrin to Poly(ethylenimine), J. Am. Chem. Soc, 114: 7916-7917 (1992).
Szeman et al., Complexation of Several Drugs with Water-Soluble Cyclodextrin Polymer, Chem. Pharm. Bull., 35(1 ): 282-288 (1987).
Gref, R. et al., New self-assembled nanogels based on host-guest interactions: Characterization and druq loadinq, Journal of Controlled Release, 111: 316-324 (2006).
Thatiparti, T.R. and Von Recum, H.A., Cyclodextrin Complexation for Affinity-Based Antibiotic Delivery, Macromolecular Bioscience, 1O: 82-90 (2010).

(Continued)

*Primary Examiner* — Satyanarayana R Gudibande
*Assistant Examiner* — Jia-Hai Lee
(74) *Attorney, Agent, or Firm* — Tarolli, Sundheim, Covell & Tummino LLP

(57) ABSTRACT

A therapeutic agent delivery system includes a therapeutic agent delivery platform and a therapeutic guest agent. The therapeutic agent delivery platform is capable of being implanted in a tissue being treated. The platform includes a substrate and at least one host molecule coupled to the substrate. The therapeutic guest agent is capable of reversibly coupling with the host molecule when administered to the tissue being treated. The reversible coupling is defined by the binding affinity between the host molecule and the therapeutic guest agent. The therapeutic guest agent is delivered at a rate determined by the affinity release rate between the host molecule and the therapeutic guest agent. The degradation rate of the therapeutic guest agent may be slower than the affinity release rate between the host molecule and the therapeutic guest agent.

17 Claims, 10 Drawing Sheets

(56) References Cited

OTHER PUBLICATIONS

International Search Report for PCT/US2010/037183 Dated Aug. 11, 2010.
Allard et al., "Convection-Enhanced Delivery of Nanocarriers for the Treatment of Brain Tumors", Biomaterials 30 (2009), pp. 2302-2318.
Gil-Alegre et al., Three Weeks Release BCNU Loaded Hydrophilic-PLGA Microspheres for Interstitial Chemotherapy: Development and Activity Against Human Glioblastoma Cells, Journal of Microencapsulation, Dec. 2008, 25(8): pp. 561-568.
Lesniak et al., "Local Delivery of Doxorubicin for the Treatment of Malignant Brain Tumors in Rats", Anticancer Research, 25: pp. 3825-3832 (2005).
Sipos et al., "Optimizing Interstitial Delivery of BCNU from Controlled Release Polymers for the Treatment of Brain Tumors", Cancer Chemother Pharmacol (1997) 39: pp. 383-389.
Thatiparti et al., "Cyclodextrin-Based Device Coatings for Affinity-Based Release of Antibiotics", Biomaterials 31, (2010), pp. 2335-2347.
Husain et al., "Complexation of Doxorubicin with β- and Υ-Cyclodextrins", Applied Spectroscopy, vol. 46, No. 4, 1992, pp. 652-658.

\* cited by examiner

THERAPEUTIC AGENT DELIVERY SYSTEM AND METHOD

CROSS-REFERENCE TO RELATED APPLICATIONS

This application claims the benefit from U.S. patent application Ser. No. 13/376,298, filed on May 21, 2012, which was a national stage application claiming the benefit of International Patent Application No. PCT/US10/371,183, filed on Jun. 3, 2010, which claimed the benefit of U.S. Provisional Patent Application No. 61/183,698, entitled "Therapeutic Agent Delivery System and Method," filed on Jun. 3, 2009, all of which are hereby incorporated by reference in their entirety.

STATEMENT REGARDING FEDERALLY SPONSORED RESEARCH

This work was supported, at least in part, by grant number NIH 1R25CA148052 from the Training Program in Cancer Pharmacology and National Science Foundation Award CBET-0954489 for CAREER: Research and Education Program in Affinity-Based Drug Delivery. The United States government has certain rights in this invention.

TECHNICAL FIELD

The present invention generally relates to a therapeutic system and a method for delivery, and more particularly to a therapeutic agent delivery system and related method for delivering a therapeutic agent to a desired location.

BACKGROUND

In many drug delivery applications, including the delivery of therapeutic agents, proteins, and genes, it is desirable to provide both temporal and spatial control over drug delivery or durable presence of signaling molecules. A high level of spatio-temporal control is needed to maintain the concentration of the drug at the site of action at a therapeutic level while minimizing undesirable systemic side effects. In addition to providing both controlled and targeted drug delivery; for many applications there must also exist some mechanism for protecting the therapeutic agent from in vivo degradation and inactivation. Consequently, many drug delivery systems (DDSs) composed of drug encapsulated in degradable or non-degradable polymer matrices, and micro- or nanoparticles have been developed. Encapsulating the therapeutic agent in a polymer matrix not only protects the drug from degradation, but also allows for the delivery of a large drug payload, which can be released over an extended period of time.

Drug release from such systems is typically controlled by passive diffusion from the polymer matrix, or a combination of diffusion and matrix degradation. While based on passive mechanisms for providing control over drug delivery, these systems do afford a certain degree of tunability. By altering parameters such as the polymer composition or the crosslink density the degradation rate of the matrix can be controlled. The use of DDSs with multiple layers has also been examined as a means of providing finer control over drug release. Systems that offer an even greater degree of tunability by utilizing more active mechanisms for controlling drug delivery have also been developed. These systems often use external stimuli, such as pH, ionic strength, and/or temperature to further control drug release. However, all of these systems share a number of limitations, stemming from the lack of a selective interaction between the drug and the DDS, that greatly restrict their broad efficacy across a number of different applications.

Without the ability to form selective interactions between the drug and DDS, the ability to tune the system becomes a function of the properties of the polymer matrix (e.g., pore size, degradation rate, sensitivity to changes in pH, ionic strength, or temperature, etc.), which often necessitates the development of multiple designs to meet different applications. This limitation is both inefficient and time consuming, and demonstrates the need for the development of a general platform that can be tuned to different applications independently of its properties. Furthermore, while many of the systems previously described can be used to provide control over the release of a single agent, they are limited in their ability to selectively control the release of multiple agents. The ability to selectively control the release, and thus expression, of multiple agents is especially important in tissue engineering applications that intend to recapitulate the natural tissue regeneration process. In such applications, the DDS must be able to express different bioactive agents at different time points. Thus, the DDS must contain some mechanism for providing selective control over the release of multiple agents. Finally, for the majority of implantable DDSs the drug reservoir is limited. While this may be acceptable, or even desirable for some applications, it is a major drawback for the treatment of chronic conditions (e.g. insulin delivery in diabetes). For such applications, a reloadable drug reservoir is needed. This presents a complicated design criterion as the DDS must be able to selectively interact with and bind the desired drug molecule(s) from the surrounding environment.

SUMMARY

The present invention relates to a therapeutic agent delivery system that includes a therapeutic agent delivery platform and a therapeutic guest agent. The therapeutic agent delivery platform is capable of being implanted in a tissue being treated. The platform includes a substrate and at least one host molecule coupled to the substrate. The therapeutic guest agent is capable of reversibly coupling with the host molecule when administered to the tissue being treated. The reversible coupling is defined by the binding affinity between the host molecule and the therapeutic guest agent. Depending on the nature of this reversible coupling, two scenarios can be realized. If the degradation rate of the therapeutic guest agent is slower than the affinity release rate between the host molecule and the therapeutic guest agent, then once the agent is released from the coupling, it will be available for therapeutic delivery elsewhere in the body (e.g. antibiotics, chemotherapy, etc.). If the degradation of the agent is faster than the release rate, then the reversible coupling can be used for the durable presence of a signaling molecule on a material or device (e.g. heparin, RGD, etc.). The therapeutic agent delivery platform is a capable of being reloaded with additional therapeutic agent after release of the therapeutic agent to the tissue being treated.

BRIEF DESCRIPTION OF THE FIGURES

The present invention may be more readily understood by reference to the following drawings, wherein.

DETAILED DESCRIPTION

Figure 1:
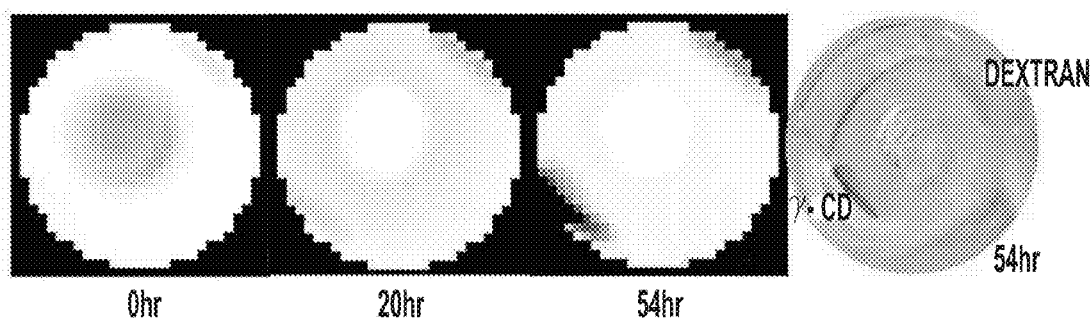
FIG. 1 provides top-down fluorescent imaging and photograph of in vitro reloading of DOX using a γ-CD and dextran polymer. Significantly higher intensity of DOX was observed in the γ-CD (lower left) than dextran polymer (upper right) 54 hr after the initial DOX injection (t=0 hr) in the center of the tissue phantom.

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such. In addition, the recitations of numerical ranges by endpoints include all numbers subsumed within that range (e.g., 1 to 5 includes 1, 1.5, 2, 2.75, 3, 3.80, 4, 5, etc.).

Treat", "treating", and "treatment", etc., as used herein, refer to any action providing a benefit to a subject afflicted with a condition or disease, including improvement in the condition through lessening or suppression of at least one symptom, delay in progression of the disease, etc.

Prevention, as used herein, refers to any action providing a benefit to a subject at risk of being afflicted with a condition or disease such as a sexually transmitted disease, including avoidance of the development of the disease or a decrease of one or more symptoms of a disease should one develop. The subject may be at risk due to exposure to the disease.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

The term subject, as used herein, refers to any animal. However, the subject is preferably a mammal, such as a domesticated farm animal (e.g., cow, horse, pig) or pet (e.g., dog, cat). More preferably, the subject is a human.

As used herein, the term "affinity" refers to the tendency of a compound to naturally associate with a region on the surface of a protein. Affinities are influenced by non-covalent intermolecular interactions between the two molecules such as hydrogen bonding, electrostatic interactions, hydrophobic and Van der Waals forces. The level of affinity is expressed by a dissociation constant, which has molar units (M) that correspond to the concentration of ligand at which the site of affinity on a particular protein is half occupied, i.e. the concentration of ligand, at which the concentration of protein with ligand bound, equals the concentration of protein with no ligand bound. The smaller the dissociation constant, the more tightly bound the ligand is, or the higher the affinity between ligand and protein. As used herein, a compound can be said to have affinity for a protein if it would have dissociation constant of at least one micromolar.

As used herein, "polypeptide" refers to a polymer of amino acids and does not imply a specific length of a polymer of amino acids. Thus, for example, the terms peptide, oligopeptide, protein, antibody, and enzyme are included within the definition of polypeptide. This term also includes polypeptides with post-expression modification, such as glycosylation (e.g., the addition of a saccharide or polysaccharide), acetylation, phosphorylation, and the like.

The present invention generally relates to a therapeutic system, and more particularly to a therapeutic agent delivery system. The therapeutic system of the present invention includes a therapeutic guest agent and a therapeutic guest agent delivery platform. The therapeutic guest agent can selectively and reversibly interact with the therapeutic guest agent delivery platform to provide finer control over therapeutic agent loading and release profiles.

In particular, the therapeutic guest agent may selectively and reversibly interact with the host molecule in the therapeutic guest agent delivery platform. The ability to form selective and reversible interactions between the therapeutic guest agent and the therapeutic guest agent delivery platform affords a number of advantages over systems that employ nonselective methods for controlling drug loading and release. By altering the type of interaction, the number of interactions, as well as the concentration and geometries of the therapeutic guest agent and the therapeutic guest agent delivery platform, in particular the host molecule, it is possible to achieve a variety of loading and release kinetics, ranging from low affinity, reversible interactions to interactions, with such high affinity that they are essentially irreversible within the lifetime of the patient or device, resulting in the durable presence of that molecule on that material. Individual interactions can also be multiplexed on a given molecule resulting in a change from low affinity to high affinity.

Additionally, the use of selective interactions between the therapeutic guest agent and the therapeutic guest agent delivery platform, in particular the host molecule, presents a facile means for providing targeted drug delivery. The loading and release kinetics of the therapeutic guest agent with the therapeutic guest agent delivery platform allows the therapeutic guest agent delivery platform to be selectively refilled or reloaded with additional therapeutic guest agents after the therapeutic guest agent has been delivered to the desired area.

A therapeutic agent delivery platform may comprise a substrate and a host molecule. The platform may be capable of, but is not limited to, being implanted in a tissue of a subject. As described in more detail below, a therapeutic guest agent, such as a polypeptide, a polynucleotide, a small molecule, an antibiotic, a steroid or an imaging agent, can include a portion capable of reversibly complexing with a host molecule attached to the substrate. Unlike other therapeutic agent delivery systems which rely solely on diffusion for therapeutic agent delivery, the reversible complexing of the host molecule and the therapeutic guest agent of the present invention is governed by molecular affinity interactions so that the degradation rate of the therapeutic guest agent may be slower than the affinity release rate of the therapeutic guest agent from the host molecule.

The therapeutic agent delivery platform may include a substrate and at least one host molecule coupled to the substrate. In one embodiment, the substrate may comprise, but is not limited to, a plurality of particles. The particles may be sized so that the particles remain substantially implanted in a desired area such as, but not limited to, tissue and do not migrate as a result of fluid flow such as, but not limited to, blood through the desired area. For example, the particles may be dimensioned so that the particles remain substantially implanted in the tissue and do not migrate to a tissue or tissues not being treated. Depending upon the particular type and location of the tissue, the particles can be dimensioned to have nanoscale (i.e., nanoparticles) or microscale (i.e., microparticles) sizes.

Where the particles comprise microparticles, for example, the microparticles can have a diameter less than about 1 mm, and typically between about 1 and 200 microns. Alternatively, where the particles comprise nanoparticles, the nanoparticles can have a diameter ranging from about less than 1 nanometer to about 1 micron. Both microparticles and nanoparticles may have, but are not limited to, an approximately spherical geometry and can be of fairly uniform size. It will be appreciated that the particles may also be larger or smaller than nanoscale or microscale sizes depending upon the particular application of the present invention.

In another embodiment the therapeutic delivery platform may be comprised of a host molecule, a substrate, or a combination thereof. The host molecule can include any molecule capable of reversibly complexing with the therapeutic guest agent such as, but not limited to, cyclic oligosaccharides. In one example of the present invention, the host molecule can comprise a CD molecule, such as an α-cyclodextrin molecule, a β-cyclodextrin molecule, a γ-cyclodextrin molecule, or a derivative thereof. As used herein, the terms "cyclodextrin" or "CD" can refer to cyclic carbohydrate molecules having six, seven, or eight glucose monomers arranged in a donut shaped ring and which are denoted α-, β-, or γ-cyclodextrin, respectively. The terms can also refer to both unmodified and modified CD monomers and polymers (i.e., CD derivatives). CD is a ring of 6-8 glucose molecules whose bonds align to form a ring-like structure having a hydrophobic pocket and a highly hydrophilic exterior. Hydrophobic small molecules can fit into the pocket of CD molecules and enter solution at a much higher concentration. Due to the reversible nature of this hydrophobic interaction, the small molecules can remain unmodified (i.e., not degraded) and can be released from the hydrophobic pocket based on molecular affinities and/or association/dissociation kinetics to exert their therapeutic effect(s).

In another embodiment the host molecule may be chemically modified CD's such as, but not limited to, hydroxypropyl-CD. The chemically modified CD may be selected due to its affinity to certain therapeutic agents.

It will be appreciated that the host molecule can include a variety of other molecules including antibodies, antibody fragments, antigens, heparin, polynucleotides, receptor proteins, avidin, streptavidin, and magnetic particles. Host molecules comprising antibodies can include whole antibodies e.g., of any isotype (IgG, IgA, IgM, IgE, etc.) and fragments thereof which are specifically reactive with a target agent. Antibodies can be fragmented using conventional techniques, and the fragments screened for utility and/or interaction with a specific epitope of interest. Thus, antibodies can include segments of proteolytically-cleaved or recombinantly-prepared portions of an antibody molecule that are capable of selectively reacting with a certain target agent. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. Antibodies can also include polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies.

Host molecules comprising polynucleotides can include oligonucleotides, nucleotides, or a fragment thereof, DNA or RNA (e.g., mRNA, rRNA, tRNA) of genomic or synthetic origin and which may be single- or double-stranded and may represent a sense or antisense strand, peptide nucleic acids, or any DNA-like or RNA-like material of natural or synthetic origin including, e.g., iRNA and ribonucleoproteins (e.g., iRNPs).

Host molecules comprising receptors can include any protein or polypeptide having a molecular structure which is generally characterized by the selective binding of a specific substance (e.g., a ligand, receptor, or other binding domain). Exemplary receptors can include, for example, cell-surface receptors for peptide hormones, neurotransmitters, antigens, complement fragments, immunoglobulins, and cytoplasmic receptors for steroid hormones.

Host molecules can also include avidin, streptavidin, or their derivatives. Avidin (a glycoprotein from chicken egg white) and streptavidin (from *Streptomyces avidinii*) are two related proteins that bind biotin with similar dissociation constants of about $10^{-15}$ M. Avidin occurs naturally in a tetrameric form with four identical subunits, each having about 128 amino acid residues, six mannose residues, and three glucosamine residues, for a combined molecular weight of approximately 68,000. In addition to the ability of avidin and streptavidin to bind biotin, many of their physical properties are quite similar. For example, both are constructed of four non-covalently attached identical subunits, each of which bears a single biotin-binding site. The subunit $M_r$ values are very similar. Moreover, several short stretches in the sequences of the two proteins are preserved, particularly two Trp-Lys stretches that occur at approximately similar positions.

Avidin, streptavidin, and their derivatives, as well as methods for obtaining such molecules, are within the purview of those skilled in the art. For example, modified avidins have been prepared, such as N-acyl avidins, e.g., N-formyl, N-acetyl and N-succinyl avidins. These derivatives of avidin reduce the charge of the protein, but they may all be prepared via covalent attachment to the available lysines of avidin. An alternative to lysine modification is the modification of arginines on avidin. In this case, the lysines are still available for subsequent interaction. Two different derivatives of avidin which are modified in this manner are commercially available. One, EXTRAVIDIN®, can be obtained in various functionally derivatized or conjugated forms from Sigma Chemical Company (St. Louis, Mo.). A second, NEUTRALITE AVIDIN (a product of Belovo Chemicals, Bastogne, Belgium), is a deglycosylated form of avidin obtained enzymatically, which exhibits a neutral pH and bears free lysine groups for further derivatization. Other avidin derivatives include those disclosed in U.S. Pat. Nos. 6,638,508 and 6,632,929, the entire disclosures of each of which are incorporated by reference herein.

Host molecules can additionally or alternatively include magnetic particles or beads. Magnetic particles or beads can comprise particulate material having a magnetically responsive component. Examples of magnetically responsive materials can include ferromagnetic, paramagnetic, and superparamagnetic materials. Magnetic particles or beads are known in the art and can include, for example, those described in U.S. Patent Pub. Nos. 2007/0225488 A1, 2005/0272049 A1, 2004/0132044 A1, and U.S. Pat. No. 7,078,224.

When selecting a host molecule the mechanical properties of the chosen host molecule may be modified to achieve a desired mechanical property for an affinity based delivery system. Modifying the mechanical properties of a host molecule may modify the release rate of the therapeutic guest agent to the desired level. Examples of methods to modify the host molecule mechanical properties include, but are not limited to, chemical grafting of the host molecule, attaching the host molecule to the backbone of a polymer, and creating a host molecule polymer by crosslinking the host molecule or short chains thereof. Examples of mechanical properties that may be modified include, but are not limited to, stiffness, strength, ductility, brittleness, malleability, plasticity, elasticity, toughness, hardness, and combinations of two or more thereof.

In one embodiment a host molecule, such as CD, may be chemically grafted onto a substrate. This substrate may include, but is not limited to, gold, glass, iron-based metals, titanium, polymers, polyester, and combinations of two or more thereof. The mechanical properties of the host molecule become similar to that of the chosen substrate. In addition, the mechanical properties may also have a limited capacity to change.

In another embodiment a host molecule, such as CD, is attached to the backbone of another polymer. This polymer may include, but is not limited to, polyvinyl alcohol, poly (acrylic acid), or a combination of two or more thereof. The mechanical properties of the host molecule become similar to that of the chosen polymer. In addition, the mechanical properties may also have a limited capacity to change.

In another embodiment CD polymers are created by crosslinking CD or short chains thereof. In one specific embodiment, the selected CD may be, but is not limited to, β-cyclodextrin and it may be crosslinked at room temperature in which the method of crosslinking has aspects of physical crosslinking and chemical crosslinking. Adjusting the nature of the above method may create materials of different levels of stiffness to provide the desired stiffness. This method is capable of forming polymers with a range of mechanical properties. To achieve desired results it is possible to change either the chemical nature of the crosslinker, the chemistry of the crosslinker, changing the crosslinker length, or a combination of two or more thereof. Examples of possible chemical natures of a crosslinker include, but are not limited to, a mono-functional crosslinker, a di-functional crosslinker, a trifunctional crosslinker, or a combination of two or more thereof. Examples of possible crosslinker chemistry include, but are not limited to, isocyanate chemistry, carbodiimide chemistry, succinimide chemistry, maleimide chemistry, and any other crosslinker chemistry known in the art. Examples of methods to obtain a desired crosslinker length include, but are not limited to, using short and long chains of PEGs as bifunctional crosslinkers. The length of the PEG molecule affects the mechanical properties, such as stiffness, of the host molecule. Additional examples of specific crosslinkers include di- or tri-functional isocyanates (e.g., hexamethylene diisocyanate and lysine triisocyanate) and glycidyl ethers (e.g., ethylene diglycidyl ether and PEG diglycidyl ether).

The substrate to which the host molecule is coupled may comprise a polymer. In one embodiment, the polymer may be positively-charged and/or biocompatible. In one embodiment, the polymer may be formed from any one or combination of known polymerizable monomers. Biocompatible polymers may include any polymer moiety that is substantially non-toxic and does not tend to produce substantial immune responses, clotting, or other undesirable effects. Examples of suitable biocompatible polymers may include, but are not limited to, polyamines (such as polyvinylamine, polylysine, polyarginine, and polyethyleneneamine), polyols (such as polyvinylalcohol, polyethylene glycol, and polysaccharides); and poly-carboxylic acids (such as polymethacrylic acid) and the like, and combinations of two or more thereof. Because drug release from the delivery platform is governed by affinity rather than polymer degradation, the polymers used can be non-biodegradable.

The amount of host molecule that is coupled to the substrate can vary in different embodiments of the invention. The amount of host molecule relative to the amount of substrate can vary from 1% to 99% by weight, and any of the other percentages included therebetween. For example, in some embodiments, the delivery vehicle includes 10%, 20%, 30%, 40%, 50%, 60%, 70%, 80%, or 90% host molecule (e.g., cyclodextrin) relative to substrate (e.g., polymer).

The substrate may also comprise at least one of, but is not limited to, antibodies, antibody fragments, antigens, heparin, integrins, polynucleotides, receptor proteins, avidin, streptavidin, magnetic particles, and the like.

Host molecules may be coupled directly with the polymer via any one or combination of known molecular interactions, including electrostatic interactions, metal coordination, covalent bonding, non-covalent interactions, hydrophobic interactions, hydrogen bonding, ionic forces, van der Waals forces and combinations of two or more thereof. It will be appreciated that the polymer, the host molecule, or both, can be chemically modified to modulate the molecular interaction(s) between the polymer surface and the host molecule. By adding a known functional group to the surface of the polymer that binds a particular host molecule, for example, the molecular interaction(s) between host molecules and the surface of the polymer can be increased.

In one example of the present invention, a CD molecule may be coupled directly with the polymer via electrostatic interactions between the negatively-charged hydroxyl groups of the CD molecule and the positively-charged polymer. The CD molecule can also be chemically modified to facilitate coupling of the CD molecule with the polymer by replacing, for example, a hydroxyl group of the CD molecule with a thiol group. Additionally or alternatively, a bifunctional cross-linker, such as PMPI can be used to facilitate coupling of the CD molecule and the polymer. Other methods of chemically coupling a host molecule to a surface can include CD-thiols attaching to gold, CD-silanes attaching to glass and/or ceramics, CD-phosphates attaching to titanium, and CD-catechols or other diols attaching to iron-containing compounds (e.g., steel).

In one embodiment, the therapeutic guest agent may include a portion for coupling to a portion of the host molecule. The portion of the therapeutic guest agent and/or the portion of the host molecule may include, but is not limited to, a portion of a molecule, a hydrophobic linker coupled to the therapeutic guest agent, or a combination thereof. In one embodiment, the therapeutic guest can include a hydrophobic portion for coupling to a CD molecule.

A therapeutic guest agent may be any agent that is desired to be provided to a specific area, as released by the host molecule. Such therapeutic guest agents may include, but are not limited to, polypeptides (e.g., growth factors, antibodies, etc.), polynucleotides, small molecules, and imaging agents, and combinations of two or more thereof. The therapeutic agent delivery system may also include more than one therapeutic guest agent that are the same as or different from the other therapeutic guest agents. The therapeutic guest agent administered will be one suitable for the treatment of the disease or condition being treated. For example, in the case of cancer treatment, the therapeutic guest agent will be an anticancer agent. The therapeutic guest agent may also comprise any one or combination of two or more of the following, many of which are anticancer agents:

Alkaloids including, but not limited to, docetaxel, etoposide, irinotecan, paclitaxel (TAXOL), teniposide, topotecan, vinblastine, vincristine, and vindesine;

Alkylating agents including, but not limited to, busulfan, improsulfan, piposulfan, benzodepa, carboquone, meturedepa, uredepa, altretamine, triethylenemelamine, triethylenephosphoramide, triethylenethiophosphoramide, chlorambucil, chloranaphazine, cyclophosphamide, estramustine, ifosfamide, mechlorethamine, mechlorethamine oxide HCl, melphalan novemebichin, perfosfamide phenesterine, prednimustine, trofosfamide, uracil mustard, carmustine, chlorozotocin, fotemustine, lomustine, nimustine, semustine ranimustine, dacarbazine, mannomustine, mitobronitol, mitolactol, pipobroman, and temozolomide;

Antibiotics and analogs thereof including, but not limited to, aclacinomycins, actinomycins, anthramycin, azaserine, bleomycins, cactinomycin, carubicin, carzinophilin, cromomycins, dactinomycins, daunorubicin, 6-diazo-5-oxo-1-norleucine, doxorubicin, epirubicin, idarubicin, menogaril, mitomycins, mycophenolic acid, nogalamycine, olivomycins, peplomycin, pirarubicin, plicamycin, porfiromycin, puromycine, streptonigrin, streptozocin, tubercidin, zinostatin, and zorubicin;

Antimetabolites including, but not limited to, denopterin, edatrexate, mercaptopurine (6-MP), methotrexate, piritrexim, pteropterin, pentostatin (2'-DCF), tomudex, trimetrexate, cladridine, fludarabine, thiamiprine, ancitabine, azacitidine, 6-azauridine, carmofur, cytarabine, doxifluridine, emitefur, floxuridine, fluorouracil, gemcitabine, tegafur, hydroxyurea and urethan;

Platinum complexes including, but not limited to, caroplatin, cisplatin, miboplatin, and oxaliplatin;

Pyrimidine and purine antagonists including, but not limited to, fluorouracil (5-FU), fluorodeoxyuridine (5-FUDR), azacytidine (5-AZC), 6-thioguanine (6-TG), chlorodeoxyadenosine (2-CDA); and Other agents including, but not limited to, aceglatone, amsacrine, bisantrene, defosfamide, demecolcine, diaziquone, eflornithine, elliptinium acetate, etoglucid, etoposide, fenretinide, gallium nitrate, hydroxyurea, lonidamine, miltefosine, mitoguazone, mitoxantrone, mopidamol, nitracrine, pentostatin, phenamet, podophillinic acid 2-ethylhydrazide, procarbazine, razoxane, sobuzoxane, spirogermanium, teniposide tenuazonic acid, triaziquone, and 2,2', 2''-trichlorotriethylamine.

In another embodiment, the therapeutic guest agent may comprise DNA or RNA, or a therapeutic molecule using DNA or RNA as a coupling agent. In one embodiment, when the therapeutic guest agent comprises RNA the RNA polynucleotide can include a siRNA, a microRNA, a sense RNA, an anti-sense RNA, a ribozyme, or a combination of two or more thereof. In another embodiment, when the therapeutic guest agent comprises a DNA plasmid the plasmid may include a therapeutic polynucleotide encoding a therapeutic polypeptide. It will be appreciated that the therapeutic polynucleotide can include any desired gene or gene fragment capable of promoting or causing a desirable cellular effect. In one embodiment, the desirable effect may be tumor suppression but the desirable effect may be any desirable effect known in the art. In one embodiment, when the desirable effect is tumor suppression, the therapeutic agent may be a therapeutic polynucleotide that may include a tumor suppressor gene, a chemokine gene, a cytokine gene, an antigenic gene, a cytotoxic gene, a cytostatic gene, an apoptotic gene (i.e., a pro-apoptotic gene), an anti-angiogenic gene, or a combination of two or more thereof.

In another embodiment, the therapeutic guest agent may comprise any bioactive agent capable of arresting cancer or tumor cell growth, inducing apoptosis of a cancer or tumor cell, and/or labeling a cell (cancerous or non-cancerous) in which the bioactive agent is present or otherwise associated with, inducing an immune response in a subject, arresting or preventing microbial growth and/or proliferation, and increasing or decreasing transcription or translation in a cell.

In another embodiment the therapeutic guest agent may also include an imaging agent. Generally, an imaging agent may include any compound used to detect, image and/or monitor the presence and/or progression of a condition(s), pathological disorder(s) and/or disease(s). Imaging agents may be used for any use known in the art such as, but not limited to, studying a wide range of physiologic processes, disease diagnosis, disease prognosis, diagnostic procedures, and the broader study of biological systems.

The substrate of the therapeutic agent delivery system may be selectively varied or modified to control the temporal and spatial delivery aspects of the therapeutic guest agent. The distribution (e.g., the number) of host molecules coupled with the substrate can be increased or decreased depending upon the desired spatial and temporal release profile for a given therapeutic guest agent (or agents). For example, a greater number of host molecules can be coupled with the surface of the substrate to promote a higher concentration, and thus spatial distribution, of therapeutic guest agents.

In one embodiment, the affinity interaction between the therapeutic agent and the host molecule may depend on the type of host molecule selected and the size of the hydrophobic molecules present in the therapeutic guest agent. In addition, the affinity interaction may differ because of the differing pocket sizes in the host molecule. The differing pocket sizes enable the host molecule to accommodate various sizes of therapeutic guest agent molecules with varying release rates. The release rate of the therapeutic guest agent may depend on the affinity interaction between the therapeutic guest agent and the host molecule. In one specific embodiment the therapeutic guest agent release rate may depend on how the therapeutic guest agent fits in the pocket. In some embodiments, a plurality of host molecules (e.g., cyclodextrin) define a plurality of pockets.

In one embodiment, $\alpha$-cyclodextrin, which has the smallest cavity size of the group containing a $\alpha$-cyclodextrin molecule, $\beta$-cyclodextrin molecule, and $\gamma$-cyclodextrin molecule, may accommodate smaller portions of hydrophobic groups present in a therapeutic guest agent or a hydrophobic unit having a similar size as that of the cavity size of the $\alpha$-cyclodextrin. While $\gamma$-cyclodextrin has the largest cavity size that can accommodate larger hydrophobic groups if present in the therapeutic guest agent. $\beta$-cyclodextrin cavity size falls in between $\alpha$-cyclodextrin and $\gamma$-cyclodextrin and accommodates accordingly.

In another embodiment, the therapeutic guest agent delivery platform may be selected due to the stiffness of the therapeutic delivery platform. In one embodiment, therapeutic guest agent delivery platforms with low stiffness may include, but are not limited to gels such as hydrogels. Stiffness in a therapeutic delivery platform may be changed by a variety of ways. Examples of ways to modify stiffness in a therapeutic delivery platform include, but is not limited to, the time of crosslinking, type of crosslinker, size of crosslinker, concentration of crosslinker, chemical conjugation, and the number/type of physical interaction such as, but not limited to, clay or ionic charge interactions.

In one example, the stiffness of the room temperature crosslinked gels is proportional to the time of crosslinking. The longer the time of crosslinking, the greater the stiffness of the gel. In another example, gel stiffness may also be dependent on the type of crosslinker. A branched crosslinker gives gels that have less stiffness while linear hydrophobic crosslinkers give gels with more stiffness. In one embodiment, in linear hydrophobic crosslinkers, hydrophobic interactions within the crosslinker as well as with CD molecules may lead to increased stiffness of the gels. In one embodiment, the above crosslinking may be possible in gels crosslinked at room temperature and is the result of allowing enough time for conformational change to occur, the formation of hydrogen bonds, and hydrophobic interactions. The above combinations may have a dramatic effect on stiffness and therefore modulate CD measured stiffness from kPa to MPa.

In one embodiment, for orthopedic applications, the desired stiffness falls in the range of kPa to MPa.

In one embodiment, when the therapeutic guest agent is a hydrophobic drug the affinity-based release may depend on either one of or both the structure of the therapeutic agent and the stiffness of the therapeutic delivery platform. In one example, if the therapeutic guest agent is a drug that fits exactly within a host molecule pocket, such as CD, and is coupled with a stiffness that is high enough, it may be very difficult for the drug to escape from the therapeutic delivery platform as the interaction between the drug and host molecule is intensified.

Other ways to alter the chemical nature of the pocket include, but are not limited to, using other kinds of molecular affinity interactions such as protein-protein interactions such as receptor-ligand interactions and antibody-antigen interactions, using oligonucleotide interactions of complimentary strands, using heparin-growth factor interactions, using avidin-biotin interactions, and other similar interactions known in the art.

To further modulate delivery and release of therapeutic guest agents to and from host molecules, therapeutic guest agents can be chemically modified with a tuning molecule. By altering the type of monovalent interaction, the number of interactions, as well as the concentration and geometry of both the host and therapeutic guest molecules, it is possible to modulate or fine-tune the binding strength, and thus the kinetics, of the host molecule-therapeutic guest agent interaction so that the complete range from highly-reversible monovalent interactions to highly-stable (and even irreversible) polyvalent interactions can be achieved. For example, by tethering multiple monovalent therapeutic guest agents together using a tuning molecule to form a multivalent therapeutic guest agent, it is possible to increase the overall binding affinity (i.e., the avidity) between a host molecule and a therapeutic guest agent.

The release rate may be altered by changing the chemical nature of the therapeutic agent or by inserting an inert molecule that fits within the host molecule but can be conjugated to the therapeutic guest agent. This allows any therapeutic guest agent to be used with an affinity-based system, even if that therapeutic guest agent has no affinities itself. In one embodiment, multiple inert molecules may be connected to a therapeutic guest agent to change the release rate to the desired result.

The release rate of the therapeutic guest agent is minimally affected by the thinness of the therapeutic delivery platform.

Therapeutic guest agents may contain multiple affinity domains. Therapeutic agents may be modified so the therapeutic guest agent has a higher binding constant compared to its pure form. In one example, rifampin, a specific antibiotic, may be modified that results in a drug version that has a higher binding constant compared to the pure antibiotic.

More than one therapeutic delivery platform may be used at a time. In one embodiment, at least two separate host molecules may be tuned to have at least two different therapeutic guest agents release at desired rates from a device. Such as, but not limited to, a small therapeutic guest agent being released from a small pocket from a host molecule and a larger therapeutic guest agent being released from a larger pocket from a second host molecule. In one example, this may be used for the synergistic release of at least two antibiotics, but may also be used for two anticancer drugs, or two of any other therapeutic guest agent listed.

The tuning molecule may include a hydrophobic molecule, such as adamantane (or a portion thereof) that is capable of coupling with a hydrophobic portion of a host molecule (e.g., the hydrophobic pocket of a CD molecule). Adamantane consists of four cyclohexanes fused to each other in chair conformations. Because adamantane is generally hydrophobic, an adamantane molecule (or a portion thereof) can be readily coupled with both the hydrophobic pocket of a CD molecule and a therapeutic guest agent. A hydrophobic tuning molecule, such as adamantane can facilitate coupling of less hydrophobic and/or hydrophilic therapeutic guest agents with host molecules that may not readily couple with a hydrophobic portion of a host molecule. In one example, as the number of adamantane molecules increase per therapeutic guest agent molecule, less therapeutic guest agent is released. The tuning molecule may consist of adamantane or more suitable hydrophobic units that have a higher binding constant with the selected host molecule to improve the sustained release properties of the therapeutic guest agents.

In one embodiment, enough tuning molecule may be added to the host molecule to make the affinity between the host molecule and the therapeutic guest agent so high that the therapeutic guest agent essentially never releases before the therapeutic guest agent degrades. In one example, in an experimental drug using CD as the host molecule and adamantane as the tuning molecule, the above result was reached with about 6 adamantane groups per drug molecule. This high affinity situation may be used in examples such as, but not limited to, self-assembling bio-active agents on the surface of an implant, refilling, renewing, and reloading similar to the drug delivery version.

It will be appreciated that the tuning molecule can comprise other molecules capable of facilitating coupling between the therapeutic guest agents and the host molecules. For example, stimuli response polymers, such as NIPAAm can be coupled with the therapeutic guest agents to permit selective release of the therapeutic guest agents from the host molecules. NIPAAm molecules contain a hydrophilic group (i.e., an amido-group) and a hydrophobic group (i.e., an isopropyl-group). NIPAAm molecules can change their overall hydrophobicity or hydrophilicity in response to a change in temperatures above or below a critical temperature of about 32° C. For example, a temperature of about 37° C. can yield generally hydrophobic NIPAAm molecules, while a temperature of about 25° C. can yield generally hydrophilic NIPAAm molecules. By selectively adjusting the temperature, the hydrophobicity or hydrophilcity of NIPAAm molecules coupled with therapeutic guest agents can be manipulated so that the NIPAAm molecules are coupled with host molecules at body temperature (i.e., 37° C.) and can then be released from the host molecules at a temperature of about 25° C.

Besides providing a means for coupling therapeutic guest agents with host molecules, the tuning molecule can also be used to establish a gradient release profile for the therapeutic guest agents. For example, a therapeutic guest agent can be coupled to a plurality of tuning molecules so that the tuning molecules couple with a respective plurality of host molecules. With this arrangement, release of the tuning molecules from the host molecules permits only the release of the therapeutic guest agent and thus a slower release profile (as compared to a single therapeutic guest agent/tuning molecule complex) can be established.

Release of the therapeutic guest agents from host molecules can also be selectively controlled by flooding implanted substrates of the therapeutic agent delivery platform with tuning molecules. Where therapeutic guest agents are coupled with hydrophobic tuning molecules, for example, a plurality (i.e., excess) of non-coupled hydrophobic tuning molecules can be contacted with the implanted particles. Contacting the implanted particles with an excess of hydrophobic tuning molecules can dislodge or separate the therapeutic guest agents from the host molecules and cause the release of the therapeutic guest agents.

Additionally, release of the therapeutic guest agents from host molecules can be selectively controlled by flooding implanted particles with additional and/or different therapeutic guest molecules having greater hydrophobicities. For example, implanted substrates can be flooded with therapeutic guest agents that are more hydrophobic than the therapeutic guest agents already coupled with host molecules. Consequently, the therapeutic guest molecules having a greater hydrophobicity can displace the less hydrophobic therapeutic guest molecules from the host molecules.

Advantageously, once the therapeutic agent has been released to the tissue being treated, the therapeutic agent delivery platform can be reloaded or refilled with additional therapeutic agents for subsequent or continuing treatment of the tissue. The therapeutic agent delivery platform can be refilled by contacting the therapeutic agent delivery platform with an additional concentration of therapeutic agents. Delivery of the therapeutic agent to the therapeutic agent delivery platform can be performed, for example, by direct injection of the therapeutic agent at the tissue site the substrate is implanted or by systemic administration of therapeutic agent to the subject. The binding affinity of the therapeutic agent to the host molecules can be such that the therapeutic agent localizes to the therapeutic agent delivery platform after systematic administration to the subject remains localized at the tissue being treated.

In an example of the present invention, a host molecule comprising CD can be made suitable for coupling to at least one surface of a polymer by first converting one of the hydroxyl groups of the CD molecule into a thiol group. This can be done by mixing about 0.300 g of 6-Tosyl-β-CD and about 0.300 g of thiourea (at about 1:16.5 molar ratio) in a 50 ml round bottom flask. Next, about 15 ml of about 80% methanol can be added to the flask. The mixture can then be heated under reflux for about 2 days at about 100° C. The mixture can be evaporated in a vacuum, whereafter about 4.5 ml of 100% methanol can be added and refluxed for about 1 hour. The solid can be filtered and dissolved in about 10.35 ml of about 10% NaOH at about 50° C. for about 5 hours. The pH of solution can be adjusted to about 2 using about 10% HCl. Next, about 0.750 ml of Trichloroethylene can be added and stirred overnight. The resulting precipitate can then be filtered and washed with water. The precipitate can be evaporated in a vacuum, followed by repeated recrystallization from water.

After converting one of the hydroxyl groups of the CD molecule to a thiol group, the thiol-modified CD molecule can optionally include a bifunctional cross-linker, such as PMPI. This can be done by dissolving about 0.750 g of EVOH in about 14 ml of DMSO. Next, about 50 mg (0.23 mmol) of PMPI can be dissolved in about 1 ml of DMSO. This solution of PMPI in DMSO can then be added to the polymer melt. The solution can react for about 3 hours at about room temperature under constant stirring.

About 12.5 mg (0.024 mmol) of the thiol-modified CD molecule can then be dissolved in about 1.25 ml of about 0.1 M NaOH (in DMSO) and incubated at about room temperature for approximately 15 minutes. About 17.5 µl of about 6 M HCl can then be added in order to neutralize the solution. The solution can be buffered with about 0.25 ml of about 0.5 M sodium phosphate. The pH of the solution can then be adjusted to approximately 7 using about 6 M HCl.

About 10 ml of the EVOH-PMPI solution in DMSO can then be removed and placed in a glass vial. The activated, thiol-modified CD molecule can then be added to the remaining 5 ml of EVOH-PMPI solution in DMSO. The solution can react for about 8 hours at about room temperature and under constant stirring. The resulting pEVOH/thiol-modified CD molecule mixture can then be electrospun into nanofiber meshes as disclosed by Kenawy et al., "Electrospinning of poly(ethylene-co-vinyl alcohol) fibers" (2003); Biomaterials 24(6):907-913.

In another example of the present invention, a therapeutic agent delivery system can comprise a polymer coupled with a heparin or heparin sulfate host molecule and a therapeutic guest agent comprising a growth factor, such as IL-7. The heparin host molecules can be chemically attached to the polymer or entangled within the polymer so that the heparin molecules do not detach before the IL-7 molecules are released from the heparin molecules. Such a therapeutic agent delivery system may be useful in treating a variety of diseases or conditions. To treat HIV/AIDS, for example, the therapeutic agent delivery system can be administered to a subject who is either infected with or suspected of having HIV/AIDS. Once administered to the subject, the IL-7 molecules can be degraded at a rate that is slower than the affinity release rate of IL-7 from the heparin molecules. Degradation and release of IL-7 in this manner can augment T cell response and thereby help to prevent or suppress HIV infection/AIDS. IL-7 can be periodically re-administered to the subject to "re-fill" the heparin host molecules and thereby maintain a substantially uniform release rate of IL-7 into the subject.

In accordance with another aspect of the present invention, a method for delivering a therapeutic agent by placing a therapeutic agent delivery system at a desired location. The therapeutic agent delivery system can comprise a therapeutic agent delivery platform. Therapeutic agent delivery platform can have a substrate and at least one host molecule coupled to the substrate. The therapeutic agent delivery system can also comprise a therapeutic guest agent capable of reversibly complexing with the host molecule when administered to the tissue being treated. The therapeutic guest agent may have a degradation rate that is slower than the affinity release rate of the therapeutic guest agent from the host molecule.

In accordance with another aspect of the present invention, a method for treating a tissue of a subject may comprise administering a therapeutic agent delivery system to a tissue target site in the subject. The therapeutic agent delivery system can comprise a therapeutic agent delivery platform. Therapeutic agent delivery platform can have a substrate and at least one host molecule coupled to the substrate. The therapeutic agent delivery system can also comprise a therapeutic guest agent capable of reversibly complexing with the host molecule when administered to the tissue being treated.

The therapeutic guest agent may have a degradation rate that is slower than the affinity release rate of the therapeutic guest agent from the host molecule.

The target tissue site can comprise any anatomical location of the subject. Examples of target tissue sites can include tissue, such as connective tissue, epithelium, muscle, and nervous tissues, as well as tumors, organs, lymph nodes, individual cells, arteries and veins. Target tissue sites can also comprise intravascular locations, such as an intra-arterial site, as well as intraluminal locations, such as a portion of the esophagus or bile duct. The implantable therapeutic agent delivery system can be implanted at the target tissue site using any known surgical, transvascular, percutaneous, and/or minimally invasive technique.

In one example, the substrate can include a plurality of particles that are formed by electrospinning. Methods for electrospinning monomers to form three-dimensional polymer-based materials are known in the art. Generally, electrospinning uses an electrical charge to form a mat of fine fibers. One setup for electrospinning can consist of a spinneret with a metallic needle, a syringe pump, a high-voltage power supply, and a grounded collector. A polymer, sol-gel, composite solution (or melt) can be loaded into the syringe and this liquid then driven to the needle tip by a syringe pump, forming a droplet at the tip. When a voltage is applied to the needle, the droplet can be first stretched into a structure called the Taylor cone. If the viscosity of the material is sufficiently high, varicose breakup does not occur (if it does, droplets are electrosprayed) and an electrified liquid jet is formed. The jet is can then be elongated and whipped continuously by electrostatic repulsion until it is deposited on the grounded collector. Whipping due to a bending instability in the electrified jet and concomitant evaporation of solvent (and, in some cases reaction of the materials in the jet with the environment) can allow this jet to be stretched to nanometer-scale diameters. The elongation by bending instability can result in the fabrication of uniform fibers with nanometer-scale diameters.

The therapeutic delivery system can also include a therapeutic guest agent, such as paclitaxel that can reversibly complex with the host molecules. It will be appreciated that the therapeutic guest agent can be dispersed on or within the particles before, during, or after electro spinning.

After forming the particles, a therapeutically effective amount of the particles can be implanted in a tissue of the subject. For example, a therapeutically effective amount of the particles can be injected into the subject at a target site tissue site. Where the target tissue site is a pulmonary tumor, for example, the tumoral target site can comprise the tissue of the pulmonary tumor itself. In this case, a therapeutically effective amount of the particles can be directly implanted at the tumoral target site via an intratumoral injection. It should be appreciated that the particles can be implanted in the subject via other suitable routes and using other suitable methods as well, such as intravenous, subcutaneous, intraperitoneal, transdermal, oral, and minimally invasive surgical routes.

It should also be appreciated that the particles can be administered to the subject without a carrier or, alternatively, as part of a pharmaceutically acceptable composition. The phrase "pharmaceutically acceptable" should be understood to mean a material (i.e., a nanoparticle) which is not biologically or otherwise undesirable, i.e., the material may be incorporated into a pharmaceutical composition administered to a subject without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration.

Using a syringe or other similar device, the particles can be directly injected into the tissue site of the subject. Where the target tissue is a tumor, upon injection into the tumor, the particles can selectively accumulate in the tumor tissue due to the high permeability of the tumor vasculature. As the tumor develops, the permeability of the tumor can decrease and thereby cause the particles to remain embedded in the tumor tissue. Accumulation of the particles in the tumor tissue can be monitored by CT scan where, for example, the particles include an imaging agent. Once the particles have been dispersed in the tumor tissue, the therapeutic guest agent (e.g., paclitaxel molecules) can begin to dissociate from the host molecules via molecular affinity interactions (i.e., association/disassociation kinetics) at an affinity release rate that is faster than the degradation rate of the therapeutic guest agent (e.g., paclitaxel molecules).

By way of example, based on previously calculated dissociation rates of paclitaxel from CD molecules and/or by monitoring tumor size (i.e., tumor regression), a desired amount of paclitaxel can be delivered to the tumor tissue. Either before, simultaneously with, or after release of paclitaxel molecules from the CD molecules, additional paclitaxel molecules can be delivered to the emptied CD molecules. A subsequent intratumoral injection of paclitaxel into the tumor tissue may be performed to "re-fill" the emptied CD molecules. Alternatively, a subsequent intravenous injection and/or oral administration of paclitaxel can be injected into the subject to "re-fill" the emptied CD molecules. Tumor size can again be assessed, and periodic doses of paclitaxel continued until the tumor has partially or entirely regressed. By administering particles capable of reversibly complexing with paclitaxel, paclitaxel (or any other therapeutic guest agent) can be localized to the tumor tissue and thereby avoid the unwanted side effects often associated with repeated systemic drug administration.

In some embodiments, the delivery platform is coated on an implantable device which is subsequently implanted in the subject to provide sustained release. The coating generally comprises the substrate (e.g., polymer) that carries the host molecule (e.g., cyclodextrin). Examples of implantable devices include various biocompatible medical devices such as screws, stents, pacemakers, etc.

In another example of the present invention, the therapeutic agent delivery platform can comprise an antibiotic-filled bandage that can be applied to a wound of a subject (e.g., following a surgical procedure). To prepare the bandage according to the present invention, at least one host molecule, such as a CD molecule can be complexed with at least one surface of a polymer that can then be applied to the bandage. As described above, CD molecules can be made suitable for coupling to at least one surface of a polymer by converting one of the hydroxyl groups of the CD molecules to a thiol group. The thiol-modified CD molecules can then be conjugated to bulk pEVOH using a bifunctional cross-linker, such as PMPI. The pEVOH/thiol-modified CD molecule mixture can then be mixed with a therapeutic agent, such as vancomycin and electrospun into nanofiber meshes (as described above). The nanofiber meshes can then be electrosprayed onto at least one surface of the bandage.

The bandage may then be placed on or around the surgical wound of the subject. Once the bandage has been securely positioned on or around the wound, the vancomycin molecules can begin to dissociate from the CD molecules via molecular affinity (i.e., association/dissociation kinetics) and permeate into and/or around the surgical wound. The vancomycin molecules can kill any bacteria present at the wound and/or prevent future bacterial infections at the wound site.

Based on previously calculated diffusion rates of vancomycin from CD molecules and/or by monitoring the wound site for infection and/or healing, an amount of vancomycin can be delivered to the bandage as needed. Either before, simultaneous with, or after release of vancomycin molecules from the CD molecules, additional vancomycin can be delivered to the emptied CD molecules. For example, a subsequent topical administration of vancomycin directly onto the bandage may be done to "re-fill" the emptied CD molecules. The wound site can again be assessed, and periodic doses of vancomycin continued until the wound site has partially or entirely healed. By providing the above-described bandage to the wound site, repeated changing of wound dressings can be avoided or minimized by periodically dosing the bandage with vancomycin.

In another example of the present invention may comprise coating implants such as, but not limited to, orthopedic implants with a therapeutic delivery platform. The therapeutic delivery platform may be a gel based platform. The therapeutic delivery platform uses a CD-based delivery system to deliver antibiotics at a desired rate. Unlike previous antibiotic coatings, the CD-based therapeutic delivery platform may be thinner than previous coatings and still deliver a therapeutic guest agent such as, but not limited to, antibiotics for a much longer duration than previous coatings. The therapeutic delivery platform may deliver a therapeutic guest agent such as, but not limited to, antibiotics for more than a month. The thinness of the therapeutic delivery platform is thin enough to not interfere with the fixation of orthopedic implants such as, but not limited to, pins, screws, K-wires, and external fixation pins. This specific example provides the ability to prevent early infection, at least 1 month, of any orthopedic implant and may be able to prevent infection for much longer periods of time. The therapeutic delivery platform may be modified to increase stiffness to better enable the coating of the therapeutic guest platform on the orthopedic implant.

A specific example of a therapeutic delivery platform that may be used in the above example are CD and dextrose-based polymers that are synthesized with lysine triisocyanate acting as the crosslinker. The polymer stiffness can easily be adjusted by adjusting crosslinker ratio. Polymers are in situ polymerized onto the fixation pins, or any desired orthopedic implant. Even though polymerization occurs rapidly, under upon heating, under about 10 minutes, the reaction is allowed to proceed for about 45 minutes. An antibiotic such as, but not limited to, novobiocin is then loaded into the crosslinked polymer disks using a solvent/solution absorption method. Novobiocin may be prepared in dimethylformamide. The antibiotic may be loaded into the coated pins by incubating the samples in the solvent at room temperature for about 4 days. The antibiotic loaded pins are then vacuum dried at room temperature.

In another example the present invention may be used to slowly deliver a therapeutic guest agent such as, but not limited to, anti-inflammatory drugs and steroids to treat joint pain, arthritis, lower back pain, and similar types of ailments. In the present example the therapeutic delivery platform may be modified to have a low stiffness to enable the therapeutic delivery platform to be in a gel form. The therapeutic guest agents may be placed within the host molecules such as, but not limited to, CD and then may be placed within viscous gels which enables the therapeutic delivery platform to be injected into the desired location such as, but not limited to, joint space. The present invention allows for sustained therapy with less frequent injections because of the slow release of the therapeutic agent. In some embodiments, the delivery platform provides a sustained release of the guest agent for at least 1 week, at least 2 weeks, at least 3 weeks, at least 4 weeks, or for at least two months.

It will be appreciated that the present invention may find application to any number of other diseases or disease conditions other than those described above. For example, the present invention may have utility in treating infectious diseases, autoimmune diseases, cancers, vaccinating against various diseases, intraocular diseases, and gene delivery/gene therapy.

Other examples of diseases or conditions treatable by the present invention can include, but are not limited to, cardiovascular diseases, e.g., atherosclerosis, coronary artery disease, hypertension, hyperlipidemia, cardiomyopathy, volume retention; neurodegenerative diseases, e.g., Alzheimer's disease, Pick's disease, dementia, delirium, Parkinson's disease, amyotrophic lateral sclerosis; neuroinflammatory diseases, e.g., viral meningitis, viral encephalitis, fungal meningitis, fungal encephalitis, multiple sclerosis, charcot joint; myasthenia gravis; orthopedic diseases, e.g., osteoarthritis, inflammatory arthritis, reflex sympathetic dystrophy, Paget's disease, osteoporosis; lymphoproliferative diseases, e.g., lymphoma, lymphoproliferative disease, Hodgkin's disease; autoimmune diseases, e.g., Graves disease, hashimoto's, takayasu's disease, kawasaki's diseases, arthritis, scleroderma, CREST syndrome, allergies, dermatitis, Henoch-schlonlein purpura, goodpasture syndrome, autoimmune thyroiditis, myasthenia gravis, Reiter's disease, lupus, rheumatoid arthritis; inflammatory and infectious diseases, e.g., sepsis, viral and fungal infections, wound healing, tuberculosis, infection, human immunodeficiency virus; pulmonary diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant related side effects such as rejection, transplant-related tachycardia, renal failure, typhlitis; transplant related bowel dysmotility, transplant-related hyperreninemia; sleep disorders, e.g., insomnia, obstructive sleep apnea, central sleep apnea; gastrointestinal disorders, e.g., hepatitis, xerostomia, bowel dysmotility, peptic ulcer disease, constipation, post-operative bowel dysmotility; inflammatory bowel disease; endocrine disorders, e.g., hypothyroidism, hyperglycemia, diabetes, obesity, syndrome X; cardiac rhythm disorders, e.g., sick sinus syndrome, bradycardia, tachycardia, QT interval prolongation arrhythmias, atrial arrhythmias, ventricular arrhythmias; genitourinary disorders, e.g., bladder dysfunction, renal failure, hyperreninemia, hepatorenal syndrome, renal tubular acidosis, erectile dysfunction; cancer; fibrosis; skin disorders, e.g., wrinkles, cutaneous vasculitis, psoriasis; aging associated diseases and conditions, e.g., shydragers, multi-system atrophy, osteoporosis, age related inflammation conditions, degenerative disorders; autonomic dysregulation diseases; e.g., headaches, concussions, post-concussive syndrome, coronary syndromes, coronary vasospasm; neurocardiogenic syncope; neurologic diseases such as epilepsy, seizures, stress, bipolar disorder, migraines and chronic headaches; conditions related to pregnancy such as amniotic fluid embolism, pregnancy-related arrhythmias, fetal stress, fetal hypoxia, eclampsia, preeclampsia; conditions that cause hypoxia, hypercarbia, hypercapnia, acidosis, acidemia, such as chronic obstructive lung disease, emphysema, cardiogenic pulmonary edema, non-cardiogenic pulmonary edema, neurogenic edema, pleural effusion, adult respiratory distress syndrome, pulmonary-renal syndromes, interstitial lung diseases, pulmonary fibrosis, and any other chronic lung disease; sudden death syndromes, e.g., sudden infant death syndrome, sudden adult death syndrome; vascular disorders, e.g., acute pulmonary embolism, chronic pulmonary embolism, deep venous thrombosis, venous thrombosis, arterial thrombosis, coagulopathy, aortic dissection, aortic aneurysm, arterial aneurysm, myocardial infarction, coronary vasospasm, cerebral vasospasm, mesenteric ischemia, arterial vasospasm, malignant hypertension; primary and secondary pulmonary hypertension, reperfusion syndrome, ischemia, cerebral vascular accident, cerebral vascular accident and transient ischemic attacks; pediatric diseases such as respiratory distress syndrome; bronchopulmonary dysplasia; Hirschprung disease; congenital megacolon, aganglionosis; ocular diseases such as glaucoma; and the like.

One aspect of the invention provides a method of treating cancer in a subject in need thereof by placing a therapeutic guest agent delivery platform at a desired location in the subject. The delivery platform includes a polymer substrate, at least one cyclodextrin host molecule coupled to the substrate, and an anticancer agent that is reversibly coupled to the host molecule. The anticancer agent is then allowed to be released from the host molecule at the desired location. Subsequently, the therapeutic guest agent delivery platform can be reloaded by contacting the therapeutic agent delivery platform with additional anticancer agent. Typically, in the case of treating a tumor, the desired location is a tumor site. In some embodiments, the release rate of the anticancer agent is adjusted by complexing a tuning molecule to one or both of the anticancer agent and the host molecule.

As used herein, the terms "tumor" or "cancer" refer to a condition characterized by anomalous rapid proliferation of abnormal cells of a subject. The abnormal cells often are referred to as "neoplastic cells," which are transformed cells that can form a solid tumor. The term "tumor" refers to an abnormal mass or population of cells (e.g., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the delivery system of the present invention include cancer is selected from the group consisting of leukemia, non-small cell lung cancer, colon cancer, central nervous system cancer, melanoma, ovarian cancer, renal cancer, prostate cancer, and breast cancer. In some embodiments, the cancer being treated is glioblastoma multiforme.

The present invention is illustrated by the following examples. It is to be understood that the particular examples, materials, amounts, and procedures are to be interpreted broadly in accordance with the scope and spirit of the invention as set forth herein.

EXAMPLES

Example 1: Reloadable Drug Delivery Implant for Localized Cancer Therapy

Glioblastoma multiforme (GBM), which involves rapid neoplasms of glial cells, is the most common form of glioma, affecting approximately 10,000 people each year in the U.S. The most malignant among all gliomas, GBM is listed as a grade IV neoplasm according to world health organization classification. As the word 'multiforme' might suggest, GBM exhibits heterogeneity in both pathology and response to treatment, contributing to its reputation as one of the most difficult cancers to treat. G. Jacob, E. B. Dinca, J Med Life 2, 386 (2009) Most GBM patients die due to cerebral edema and increased intracranial pressure within one year of diagnosis. Despite multimodal treatment with surgical resection followed by chemo- and radiotherapy, the prognosis for GBM patients has not improved significantly in the past two decades, with a medium survival of 14.6 months and 3-year survival rate of only 10%.

The dismal prognosis partly stems from the highly infiltrative nature of GBM, rendering total resection impossible, and subsequent recurrences inevitable. Wong et al., J Clin Oncol 17, 2572 (1999). Postresection chemotherapy is a standard adjuvant or stand-alone treatment option for recurrent GBM (rGBM). However, there is a lack of effective methods to administer chemotherapeutic agents to the brain. With the exception of few drugs, most notably temozolomide, systemically administered chemotherapeutic agents are ineffective due to high toxicity and the blood-brain barrier (BBB) preventing their entries into the brain. To bypass the BBB, localized chemotherapy can be provided directly at the site of tumor resection via drug-carrying nanoparticles (Allard et al., Biomaterials 30, 2302 (2009)) and polymeric implants, among which the carmustine-laden Gliadel® wafer is the most extensively characterized. Sipos et al., Cancer Chemother Pharmacol 39, 383 (1997). Although studies have shown that Gliadel® wafers increase 6-month survival by 50%, the prognosis for GBM patients remains poor. Based on two phase-III clinical trials, Gliadel® wafers, compared to placebos, increased the mean overall survival of GBM patients by a mere 2 months. Westphal et al., Acta Neurochir (Wien) 148, 269 (2006).

Aside from the well-known toxicity of carmustine to healthy brain tissue, Gliadel® wafers also lack the ability to provide chemotherapy for extended periods of time. Recurrences of GBM can occur any time between 10-180 weeks after the initial diagnosis, while Gliadel® releases near 90% of its loaded carmustine in approximately 1 week, prompting treatment ineffective against recurrences that may occur thereafter. Fung et al., Cancer Res 58, 672 (1998). A few recent studies were conducted to address some of the issues associated with Gliadel® wafers. For example, DOX-loaded polymer wafers were developed to demonstrate the feasibility of using an alternative chemotherapeutic agent. Lesniak et al., Anticancer Res 25, 3825 (2005) In another study, poly(lactic-co-glycolic acid) microspheres were used to extend the effective delivery of carmustine to 3 weeks. Gil-Alegre et al., J Microencapsul 25, 561 (2008). Unfortunately, these current studies offered only incremental improvements and not significant upgrades to Gliadel wafers. The dominant mechanism governing drug release in these systems was diffusion, which was characterized by a "burst effect," where the majority of the loaded drugs released after the first few days, thus limiting effective treatment to short periods of time. Similarly, carmustine-loaded poly(lactic-co-glycolic acid) microspheres and DOX-loaded PCCP:SA wafers exhibited significant burst release effects.

In search of a 'smarter' implantable system, the inventors engineered a polymer that can serve as both a drug delivery vehicle and as a reloadable reservoir. If tumor relapses after depletion of the initial dose, the sponge-like polymer, with specific affinity towards the drug, is reloaded via local injections of additional doses deemed appropriate for the recurrence.

To test the efficacy of the polymer, glioblastoma multiforme (GBM) was chosen as the disease model due to GBM's poor prognosis and its almost inevitable recurrences. Wong et al., J Clin Oncol 17, 2572 (1999). GBM relapses with varying tumor volume and time of recurrence, which can range between 10 to 182 weeks after initial diagnosis. Gliadel®, a commercially available implantable wafer for GBM treatment, can only deliver a fixed amount of drug at an effective concentration for up to 4 weeks. Fung et al., Pharm Res 13, 671 (1996). As a result, the dose and therapeutic period of Gliadel® are restricted by the number of implanted wafers and the time of implantation, respectively. Hereafter, the inventors demonstrate that their versatile polymer implant is capable of delivering an anticancer drug, doxorubicin (DOX), at a sustained rate over 8 weeks, which was found to be more therapeutically effective than rapid, burst delivery. In addition, it is shown that the polymer was reloadable via simple local injections, further prolonging the therapeutic window and allowing the therapy to be tailored to tumor recurrence of the individual patient.

In many embodiments of the reloadable polymer of the invention, cyclodextrin (CD), a cyclic oligosaccharide with a hydrophilic outer shell and relatively hydrophobic inner cavity, is used as the host molecule. Through the formation of inclusion complexes with small molecules, CD, in its monomer form, is used in pharmaceutical industry to improve solubility of hydrophobic drugs. Leveraging CD's affinity towards certain drugs including DOX, our laboratory developed processes using 1,6-diisocynatohexane (HDI) to crosslink CD into an insoluble polymer, which served as the platform for both the delivery and reloading of DOX. Thatiparti et al., Biomaterials 31, 2335 (2010).

Two types of CD were examined, β- and γ-CD, (7 and 8-member oligosaccharides respectively) which have different cavity diameters and potentially varying degrees of affinity towards DOX. Surface plasmon resonance and fluorometry studies showed that the association constant ($K_a$) between DOX and γ-CD was higher than that between DOX and β-CD, which is most likely attributed to a better fit of the bulky anthraquinonic nucleus of DOX in the larger γ-CD cavity. Husain et al., Appl Spectrosc 46, 652 (1992). See Table 1. To verify the formation of inclusion complex between DOX and γ-CD, Fourier transform infrared spectroscopy was performed on grounded γ-CD polymer, DOX, and grounded γ-CD polymer loaded with DOX. Peaks between 700-900 $cm^{-1}$, which represents the aromatic rings on DOX, were mostly masked in the spectrum of γ-CD loaded with DOX, suggesting formation of inclusion complex. As a non-affinity control, a third type of polymer, isocyanate crosslinked dextran, was synthesized using a similar process as that for CD. While sharing the same monosaccharide unit as CD, dextran is linear or branched in structure, so no inclusion complexes would form with DOX. Flory-Huggins interaction parameter ($\chi$) calculations revealed a 14 times higher $\chi$ between DOX and dextran than between DOX and the central cavity of CD, confirming the lack of interaction and affinity between DOX and dextran.

TABLE 1

Characterization of $K_a$ between DOX and CDs.

| Analytical Methods | Association Constant $K_a$ ($M^{-1}$) | |
|---|---|---|
|  | β-CD · DOX | γ-CD · DOX |
| Fluorometry | 153 ± 15 | 264 ± 20 |
| Surface Plasmon Resonance | 205 ± 5 | 490 ± 7 |

Figure 2:
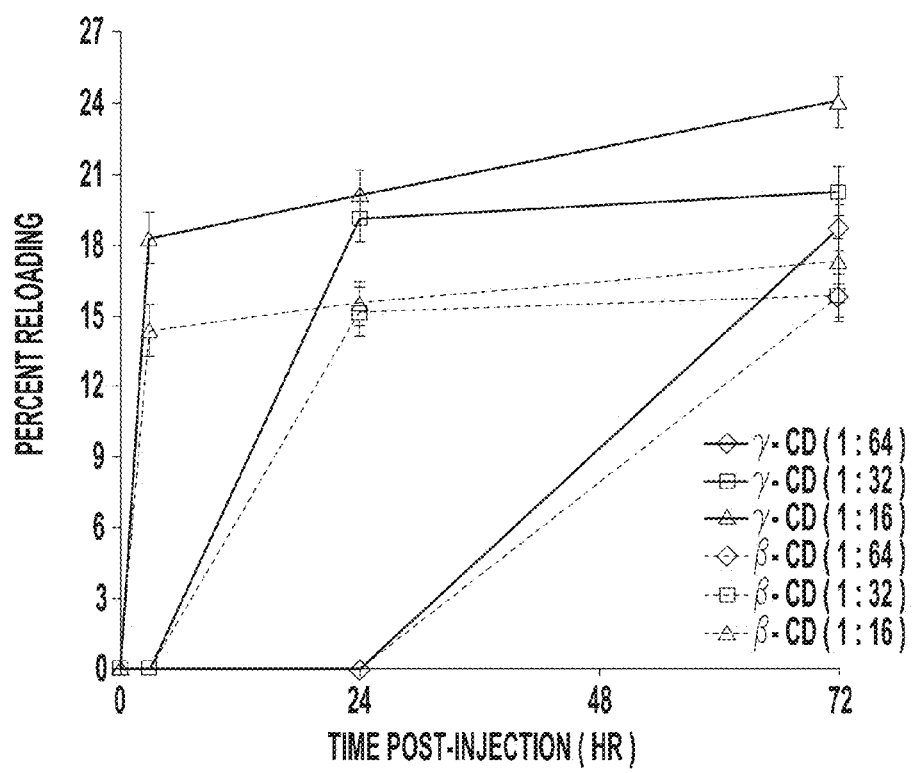
FIG. 2 provides a graph showing in vitro reloading of DOX in γ-CD and β-CD polymers with various crosslinking ratios (1:0.16, 1:0.32, and 1:0.64). Percent reloading was higher in γ-CD than β-CD polymers. In addition, loosely crosslinked polymers (1:0.16) resulted in highest percent reloading. γ-CD polymers (1:0.16) resulted in the fastest DOX reloading, which suggested that these polymers were most suitable for in vivo studies.
Figure 3:
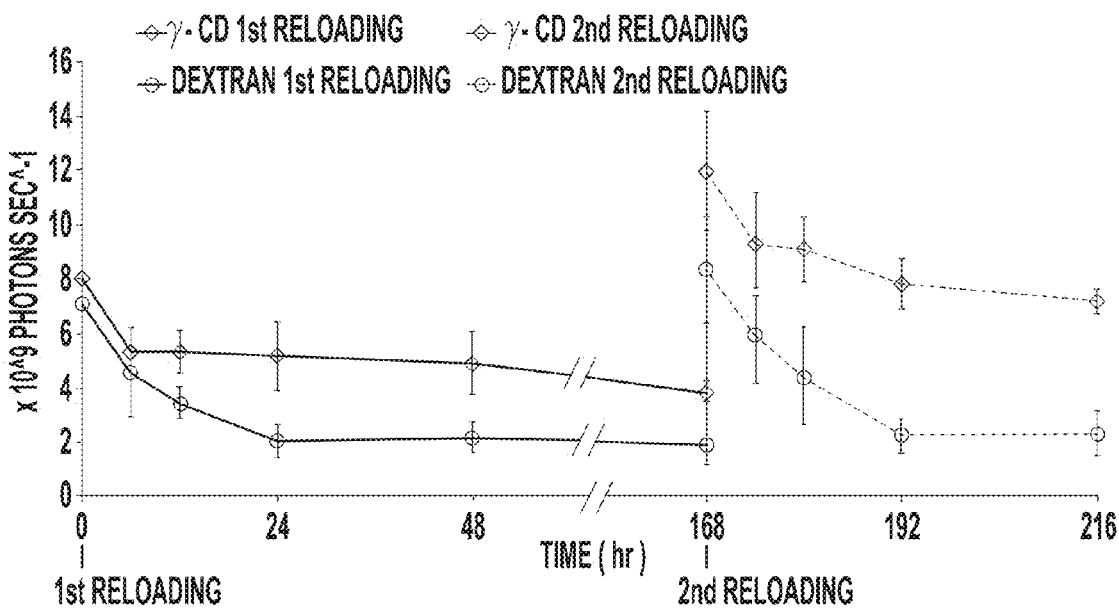
FIG. 3 provides graphs showing in vivo reloading of DOX of γ-CD and dextran polymers using two subcutaneous injections that were one week apart. γ-CD, after both DOX injections, showed higher photon flux than dextran polymers. After the initial drops in signal the decrease in flux appeared more gradual in γ-CD than dextran. In addition, the cumulative increase in fluorescence signal for γ-CD reveals the potential advantage of multiple reloading injections for affinity-based polymers.
Figure 4:
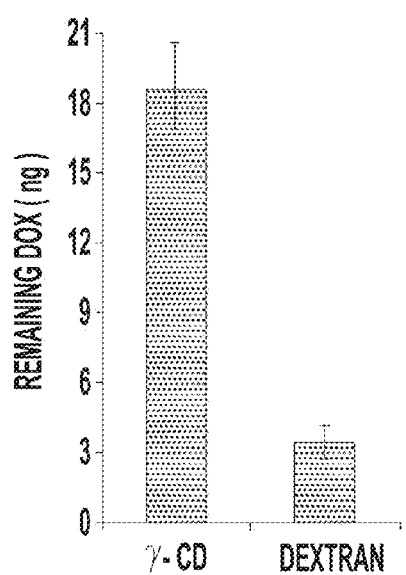
FIG. 4 provides a bar graph showing DOX extracted from surgically removed polymers at the end of in vivo reloading. At the end of the 2nd reloading period, all polymers were removed from mice and the amount of remaining DOX in the polymers was extracted using DMSO. Significantly more DOX were recovered in γ-CD than dextran polymers.

To assess whether the affinity-based polymer can be effectively reloaded, a competitive reloading assay was designed by embedding a γ-CD and a dextran polymer disk in opposite ends of an agarose tissue phantom in a closed environment and injected DOX into the center to allow the drug to freely diffuse. Top-down fluorescence imaging (FIG. 1) of the phantom showed significantly higher intensity of DOX in γ-CD than dextran after 54 hr. In a photograph of the phantom taken 54 hr post-injection of DOX, the more intense red color indicates the drug showed higher loading in γ-CD than in dextran was attributed to differences in affinity. In a higher throughput assay using image analysis, we examined how different crosslinking ratios (CD's glucopyranoside unit: HDI) affect reloading. FIG. 2 shows that the experimental condition resulting in the highest and fastest percent reloading of DOX was loosely crosslinked (1:0.16) γ-CD polymers (n=3). Finally, we implanted empty γ-CD (1:0.16) and dextran polymers (n=5) subcutaneously in the flanks of nude mice to test reloading in vivo, in the absence of tumors. At two time points that were one week apart, subcutaneous injections of 100 ng of DOX were performed near the polymer. For 48 hr after each injection, reloading was monitored using fluorescence imaging. FIG. 3 shows higher photon flux from γ-CD than dextran polymers after both injections. In both polymers, similar drops in flux during the first 6 hr post-injection were likely due to effects of systemic drug clearance. Thereafter, however, the decrease in flux appeared more gradual in γ-CD than dextran, suggesting the affinity between γ-CD and DOX facilitated reloading and potentially a new window of drug release. At the end of the $2^{nd}$ reloading period, all polymers were surgically removed and extracted the remaining DOX in dimethyl sulfoxide. Significantly more DOX was recovered from γ-CD than dextran polymer (FIG. 4).

Figure 5:
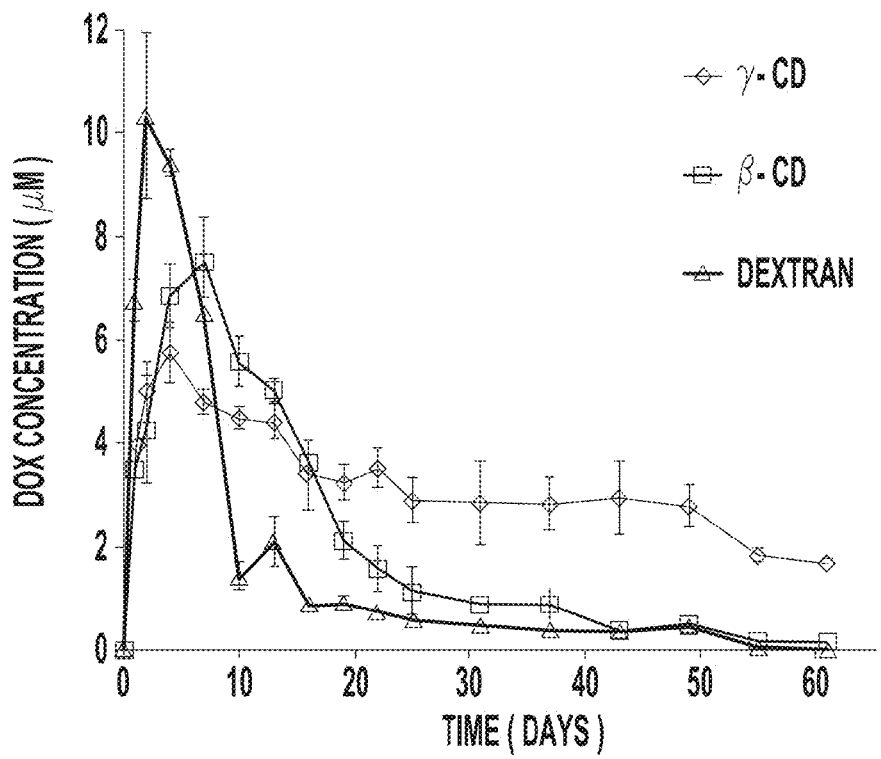
FIG. 5 provides a graph showing in vitro release of DOX. The concentration of DOX released from γ-CD polymer was above 2 μM for 61 days. In contrast, DOX released from β-CD and dextran rapidly dropped <1 μM, starting at day 25 and day 16, respectively.
Figure 6:
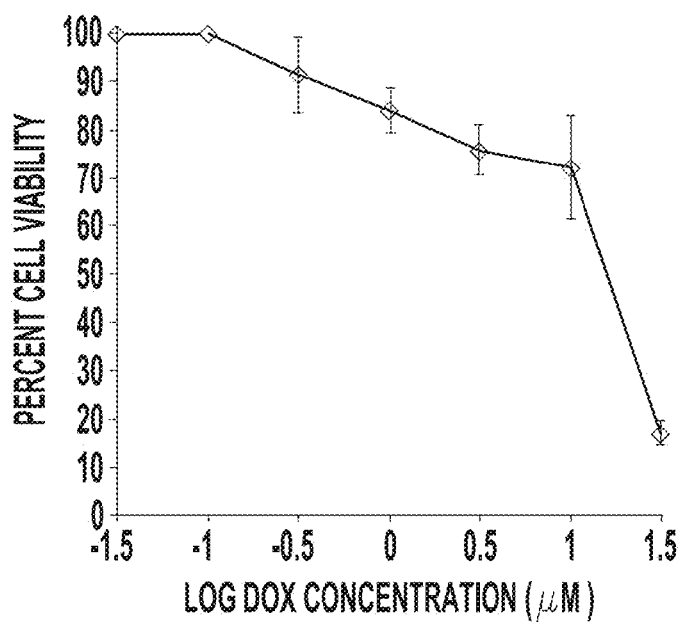
FIG. 6 provides a graph showing the cytotoxicity of DOX against U-87 MG cells.
Figure 7:
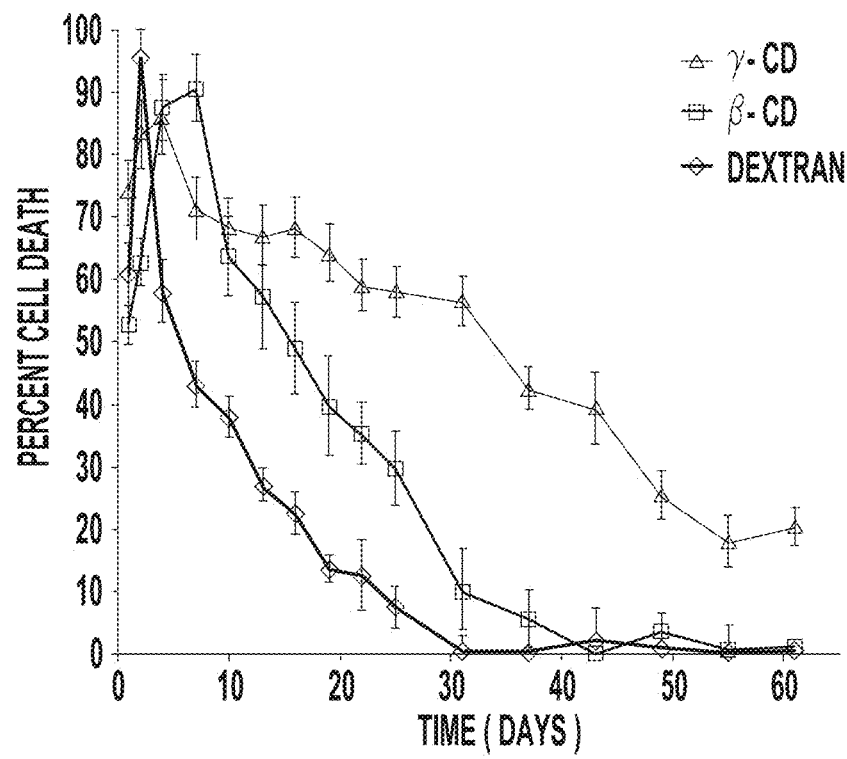
FIG. 7 provides a graph showing the capacity of daily doses from the in vitro release experiments to be able to kill LLC (Lewis Lung Carcinoma) cells. DOX was released from polymer disks of either γ-CD, β-CD, or dextran into cell culture medium for over 60 days. Medium was changed daily and daily release aliquots were stored frozen. At the end of the period, all release aliquots were thawed and incubated with LLC cells. Cell death was evaluated by MTT assay.

The inventors hypothesized that, in addition to the ability to be reloaded, the affinity-based polymer could release DOX at a sustained rate over extended period of time, similar to their observations of using this polymer to deliver other small molecule drugs. T. R. Thatiparti, H. A. von Recum, Macromolecular Bioscience 10, 82 (2010). Polymer implants such as Gliadel® release the majority of its loaded drug within the first few days, a characteristic typical of most drug delivery systems, which are dependent on drug diffusion alone. In affinity-based polymers, an additional mechanism—formation of inclusion complex between DOX and CD—can modulate drug release and essentially extend the therapeutic period of the implant. To test the hypothesis, β-CD, γ-CD, and dextran (n=3) were loaded in 4 ml of 10 mg/ml DOX solution for 72 hr before transferring to 2 ml of cell culture medium for release at 37° C. with gentle agitation. At predetermined time points, two samples were aliquoted from each release medium: one for quantifying DOX release via fluorescence spectroscopy and the other for applying to a cancer cell line in vitro to test for bioactivity of the released DOX. The release medium is then replaced with fresh medium in order to maintain sink conditions. As shown in FIG. 5, the concentration of DOX release from γ-CD was >2 µM for 61 days. In contrast, DOX released from β-CD and dextran rapidly dropped <1 µM starting at day 25 and 16, respectively. In a cytoxicity study (FIG. 6), ~20% of U-87 MG cells, a human glioblastoma cell line, was killed using 2 µM of DOX. These results indicate that γ-CD, due to its relatively high affinity towards DOX, can deliver the drug at a concentration >$IC_{20}$ for a longer time than β-CD and dextran were capable. The bioactivity of the released DOX was then confirmed by treating Lewis lung carcinoma cells with aliquots from previously mentioned release samples. FIG. 7 shows that cell killing was maintained for much longer when released from γ-CD than other polymers, which was likely due to the steady release of DOX from γ-CD (FIG. 5).

Figure 8:
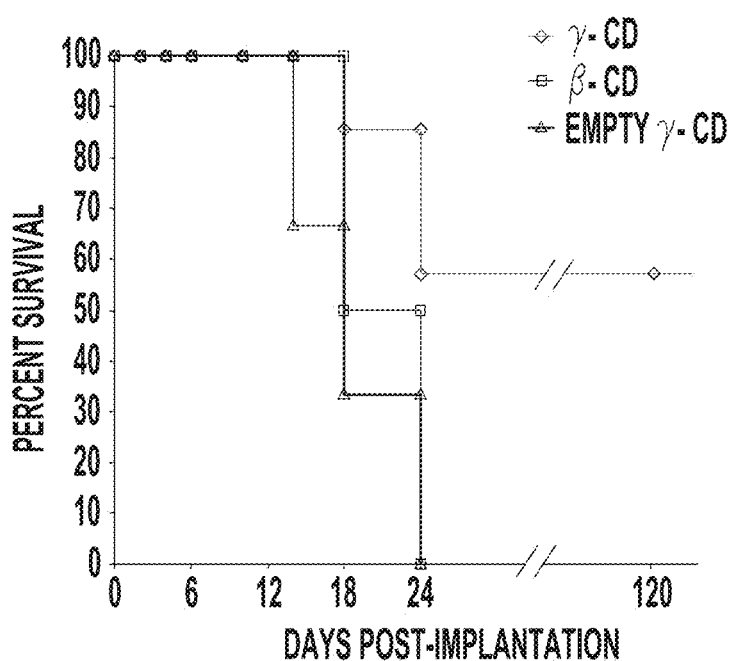
FIG. 8 provides a Kaplan-Meier survival curve showing mice implanted with U-87 MG cell tumors, and with polymer disks loaded with DOX and made from γ-CD, 13-CD, or dextran. Animals with β-CD (which shows only very low affinity to DOX), or dextran implants were rapidly overcome by tumor growing relatively unchecked, and died or were euthanized by 24 days. Animals with γ-CD implants were mostly cured, with over 50% of the animals showing no recurrence out to 120 days (even 9 months, data not shown).
Figure 9:
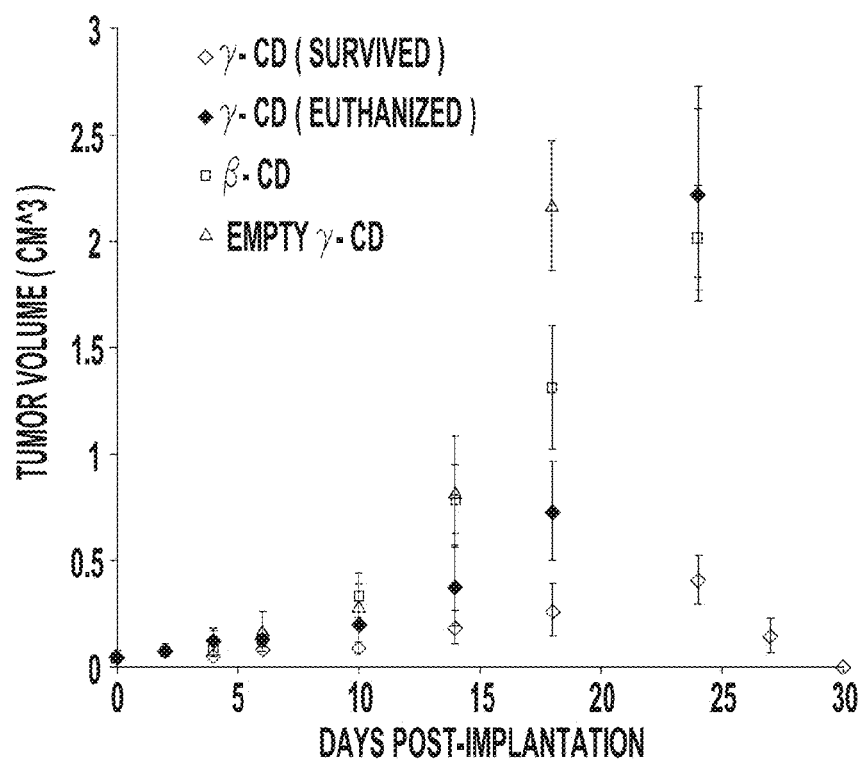
FIG. 9 provides a graph showing the tumor size of the animals evaluated in the experiments described for FIG. 8. Tumors in animals with β-CD, or dextran implants grew exponentially until the end of the study. In the animals with γ-CD implants there were two groups. The ones which were cured showed initial exponential growth followed by rapid tumor regression. In the ones in which the treatment was insufficient the tumors again grew exponentially until the endpoint.
Figure 10:
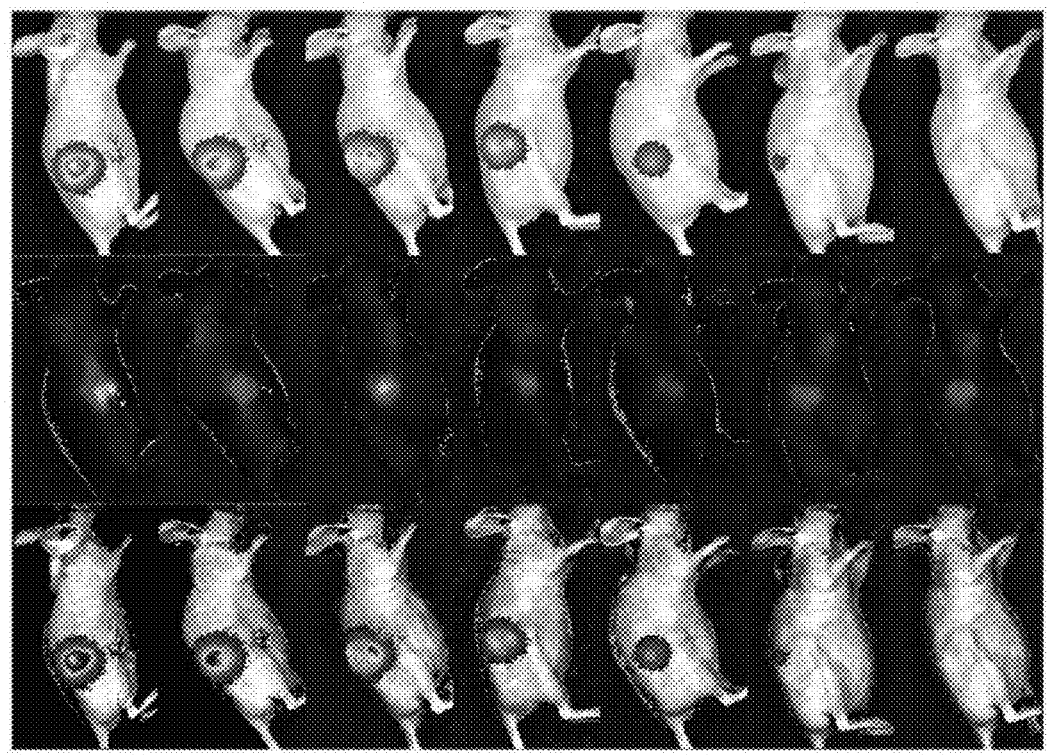
FIG. 10 provides bioluminescence and fluorescence imaging of an animal implanted with a γ-CD implant loaded with DOX, and a U-87 MG human glioblastoma cell line modified to constitutively express firefly luciferase. Top Row: Bioluminescence imaging of a single animal followed over the course of several weeks shows an initially robust tumor regressing to no detectable signal. (Control, untreated animals all show unchecked tumor growth, FIG. 8). Middle Row: Fluorescence imaging showing Dox both in the device and released into the local environment throughout the course of the study. Bottom Row: A superposition of both bioluminescence and fluorescence imaging showing that the points observed are not from the same source, but from two distinct, separately located artifacts (the tumor and the implant loaded with DOX respectively).

In vivo efficacy of delivery from the affinity-based polymer was validated in two steps: 1) demonstration of tumor clearing from affinity-based delivery; and 2) confirmation that in vivo reloading shown above was capable of clearing tumors. In demonstrating tumor clearing, a xenograft model of human GBM in mice was used. The inventors injected $0.5 \times 10^6$ luciferase expressing U-87 MG-luc2 cells in the flanks of nude mice, until tumors reached ~50 mm$^3$, at which point they surgically implanted DOX-laden (~5 mg/polymer) 13-CD (n=6) and γ-CD polymer disks (n=7) directly underneath the tumors. Empty γ-CD polymer disks (n=6) were implanted as non-drug control. A Kaplan-Meier survival curve in FIG. 8 shows more than half of the tumor-bearing mice implanted with DOX-laden γ-CD showed complete tumor regression, compared to no surviving mice implanted with DOX-laden 13-CD (Log-Rank test: p<0.041) and empty γ-CD polymers (Log-Rank test: p<0.019). The surviving mice were imaged periodically (up to 16 weeks) to ensure that tumor did not recur. Tumor volume measurements (FIG. 9) shows the surviving mice implanted with γ-CD were tumor-free by day 30, while tumors in all other conditions grew exponentially. In mice that survived the treatment, decreases in the bioluminescence intensity of tumors corresponded with decreases in the fluorescence intensity of DOX (supplementary material), demonstrating that the rate of drug release was crucial for therapeutic efficacy rather than total drug amount. One example is illustrated in FIG. 10. Even in the mice without complete tumor clearance, hematoxylin and eosin stains of tumors show necrosis in the lower central regions of the tumors, beneath which the polymers were implanted. Therefore, the polymers were partially effective even in mice that failed to survive; the efficacy could have been hampered by limited tissue penetration, suboptimal drug concentration, or tumor heterogeneity (including cancer stem cells).

Figure 11:
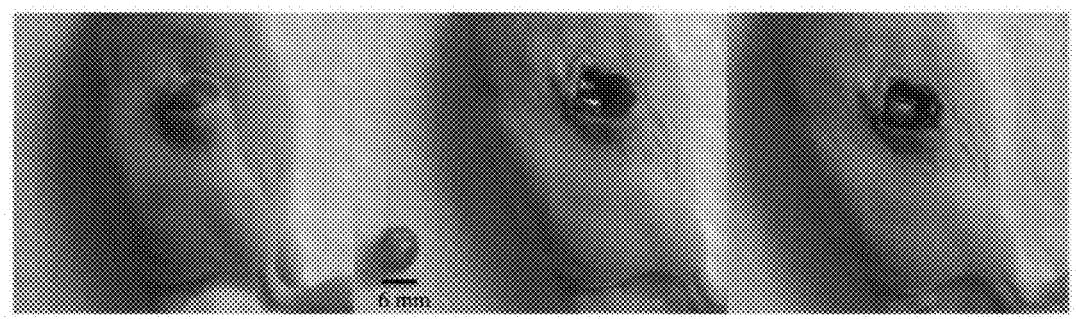
FIG. 11 provides an image showing the surgical procedure of the animal model used to test implant refilling. A tumor of U-87 MG cells is grown in the flank of athymic nude mice. When this tumor reaches 8 mm in diameter at about day 10 (first panel), the tumor is accessed surgically. A 6 mm punch is used to remove the center core of the tumor (middle panel) leaving behind a 2 mm rim of the original tumor. Into this cavity an empty implant of either γ-CD or dextran polymers. The wound is sutured shut and several days later the site is injected with either DOX or no drug (for empty, non-refilled controls).
Figure 12:
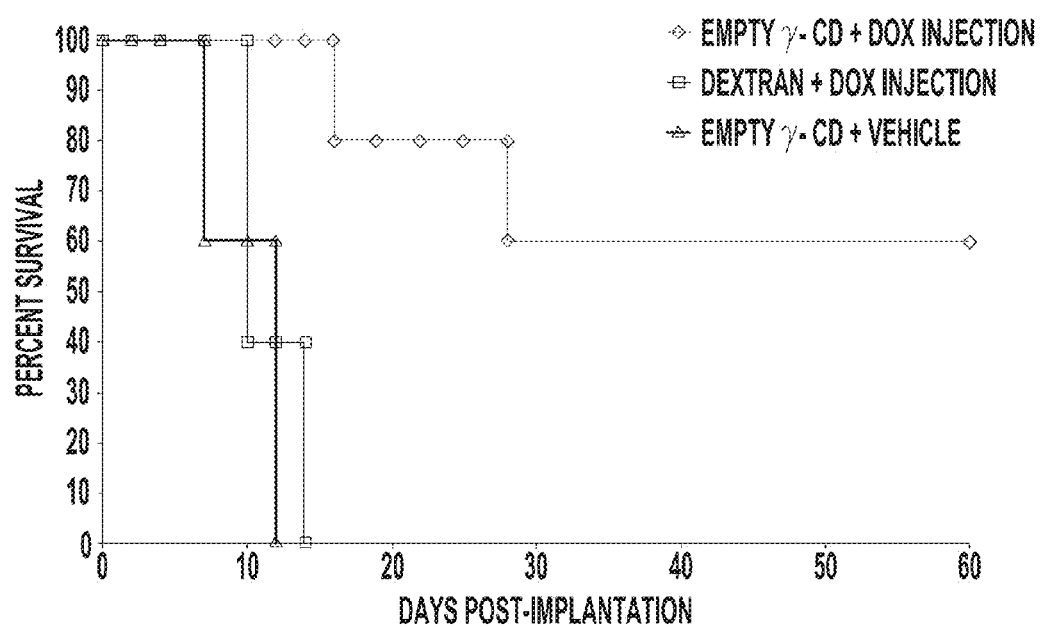
FIG. 12 provides a Kaplan-Meier survival curve of mice undergoing drug refilling in a tumor model (FIG. 10). The figure shows mice implanted with U-87 MG cells. At day 10 tumors have been punched down to a 2 mm rim, and mice were then implanted with empty polymer disks made from either γ-CD, or dextran. Animals were then injected with either 100 mM of DOX, or in one set of γ-CD injected with a sham of no drug. Animals either with γ-CD implants which were not refilled, or with dextran implants which had undergone the refilling injection were rapidly overcome by tumor growing relatively unchecked, and died or were euthanized by 14 days. Animals with γ-CD implants were mostly cured, with over 50% of the animals showing no recurrence out to 60 days.

To test the therapeutic efficacy of in vivo reloading, a treatment model was developed in mice (FIG. 11) to mimic resection surgery used in human GBM patients. In mice with size-matched tumors (~8 mm in diameter), a 6 mm biopsy punch was used to resect the central region of the tumor, creating a void where we then implanted empty γ-CD or dextran polymer disks (n=5). Mice implanted with γ-CD and no refilling did not survive past day 12 post-implantation (FIG. 12), indicating that resection alone was an insufficient treatment. Mice implanted with dextran, and injected with 100 ng of DOX for potential refilling did not survive past day 14 post-implantation, indicating that the total drug amount was insufficient, in one high dose, for treatment. While mice implanted with γ-CD and injected with the same refilling dose resulted in 60% of the mice tumor-free after 8 weeks. Additional experiments demonstrated that no recurrence occurred up to 9 months (data not shown). At this time point, approximately 5 ng of DOX/polymer disk was extracted from γ-CD removed from euthanized mice, while no traceable DOX was found in dextran polymers. These results confirm the need for sustained dosing, and indicate that reloading affinity-based polymers for further delivery effect was possible significantly improving therapeutic efficacy of post-resection cancer therapy (Log-Rank test: γ-CD vs. dextran p<0.008; γ-CD vs. vehicle p<0.006).

Implantable drug delivery systems have the advantage of delivering predictable amount of drug to desired locations in the body while minimizing systemic exposure. This affinity-based polymer is an especially attractive system with its ability to not only deliver drugs at a sustained rate for extend period of time, but also to allow for multiple periods of drug reloading as the therapeutic treatment mandates. The potential implications for cancer therapy are reduced cost and post-operative complications associated with multiple resection and implantation surgeries. Due to CD's ability to form inclusion complexes with a variety of drugs, the affinity-based polymer platform is also a viable option for treatment of other human diseases that require long-term therapy.

Materials and Methods

Fabrication of Affinity-Based Polymers

Based on specific polymer weight to solvent volume percentages and crosslinking ratios, β- and γ-CD and dextran pre-polymers were dissolved in DMF or DMSO prior to the addition of the crosslinker HDI. After mixing under room temperature for 1 min, the solution was then poured into a 10 cm Teflon® dish and heat cured at 70° C. CD and dextran polymers were formed after approximately 2 hr and 4 hr of heating, respectively. Thin disks of approximately 10 mm in diameter were punched out and washed sequentially with first the solvent, then a 1:1 solvent to water mixture, and finally water for 24 hr to remove unreacted products. All gels were UV-irradiated for 10 min prior to use.

Characterization of DOX and CD Affinity Using Fluorometry

When DOX, a fluorescent compound, forms an inclusion complex with CD, the fluorescent signal is enhanced (1) due to diminished intermolecular quenching. Increasing the amount of β- and γ-CD monomers (0 mM-16 mM) were added to a constant concentration of DOX in cell culture medium at 37° C. (n=3). Aliquots were taken for fluorescence measurements (Synergy H1) with an excitation and emission wavelength of 498 nm and 590 nm, respectively. Based on a modified Benesi-Hildebrand equation, nonlinear regression analysis was performed in MATLAB to estimate the association constants ($K_a$).

Characterization of Affinity Between DOX and CD Using Surface Plasmon Resonance

Surface plasmon resonance (SPR) spectroscopy was performed on Biacore x100 to characterize the affinity between DOX and β- and γ-CD. 6-$NH_2$-β- and γ-CD monomers were immobilized onto CM5 sensor chips using amine-coupling chemistry. To optimize immobilization conditions, pH scouting was performed via suspending 0.1 mM of 6-$NH_2$-β- and γ-CD monomers in various pH buffers (borate 8.5, HBS-N 7.4, PBS 7.4, acetate 5) and injecting the suspensions over the sensor chip surface. The carboxylic groups on the sensor chip surface were activated via n injection of 0.4

M EDC/0.1 M NHS. Surface immobilization in flow cell 2 proceeded with an injection of 0.1 mM of 6-amino-6-deoxy-β- or γ-CD monomers suspended in the previously determined optimal buffer, borate 8.5. Blank immobilization was performed in flow cell 1, which was used as a reference flow cell. Finally, unreacted reaction sites in both flow cells were inactivated by an injection of 1 M ethanolamine (pH 8.5). All injections were performed at 10 µl/ml for 7 min.

DOX samples at 1, 0.5, 0.25, 0.125, and 0.0625 mM dissolved in HBS-N buffer (pH 7.4) were injected over the CD-immobilized surface with a 2 min association and 4 min dissociation time for affinity studies. Injections of 50 mM sodium hydroxide was used to wash off any bound DOX and regenerate the sensor chip surface in between sample injections. Successful regeneration was confirmed by examining the baseline signal prior to each injection and that after regeneration. Linear regions of the DOX concentration vs. SPR response plots were identified and additional runs were made to estimate $K_a$ between DOX and β- and γ-CD using preset models in Biacore Evaluation Software.

Fourier Transform Infrared Spectroscopy

Inclusion complex formation between DOX and CD was confirmed using Fourier transform infrared spectroscopy (BioRad FTS 575C). γ-CD polymer was loaded in a 1 mg/ml DOX in PBS solution for 72 hr prior to air-drying for 72 hr. Pure γ-CD polymer was dried similarly. Then, samples of grounded pure γ-CD polymer, pure DOX, and grounded DOX-loaded γ-CD polymer were incorporated into a thin potassium bromide pellet prior to scanning. The scans were run with wavelengths from 600 cm$^{-1}$ to 4000 cm$^{-1}$.

Flory-Huggins Interaction Parameter ($\chi$)

The non-affinity control used in this study was dextran. While sharing the same monosaccharide unit as CD, dextran is linear or branched in structure, so no inclusion complexes would form with DOX. In order to confirm whether dextran would be a suitable non-affinity control, Flory-Huggins interaction parameter ($\chi$) was calculated between DOX and CD (its inclusion complex forming cavity) and DOX and dextran. Although $\chi$ parameter had been used recently to optimize the design of drug delivery polymer systems (Tian et al., Mol Pharmaceut 10, 236 (2013)), it was originally developed to characterize interactions in mixtures of small molecules, polymer-solvent systems, and polymer blends. It can be calculated based on Hildebrand's solubility parameter δ:

$$\chi_{AB} = \frac{V}{RT}(\delta_A - \delta_B)^2$$

where V is a reference volume; δ is the solubility parameter of the components; R is the universal gas constant; and T is the absolute temperature. The solubility parameter δ can be divided into three components and estimated using group contribution method:

$$\delta_t = \sqrt{\delta_d^2 + \delta_p^2 + \delta_h^2}$$

where $\delta_d$, $\delta_p$, and $\delta_h$ represent disperse forces, polar group forces, and hydrogen binding energy, respectively. These components are calculated as follows:

$$\delta_d = \frac{\sum F_d}{V};$$

$$\delta_p = \frac{\sqrt{\sum F_p^2}}{V};$$

$$\delta_h = \sqrt{\frac{\sum E_h}{V}}$$

where $F_d$ is the group contribution to the disperse forces; $F_p$ is the plane symmetry factor of polar groups; and $E_h$ is the group contribution to hydrogen bonding energy. The group contribution to these forces are found in a solubility parameter handbook by Barton. A. Barton, CRC handbook of solubility parameters and other cohesion parameters (CRC Press LLC, Boca Raton, ed. 2nd, 1991)

Solubility parameters for polymers are usually calculated using group contribution methods based on the repeating unit of the polymer. Hence in this study, δs for α-CD, β-CD, γ-CD, and dextran polymers were all calculated based on their respective monomer units.

In Vitro Reloading of DOX

Figure 13:
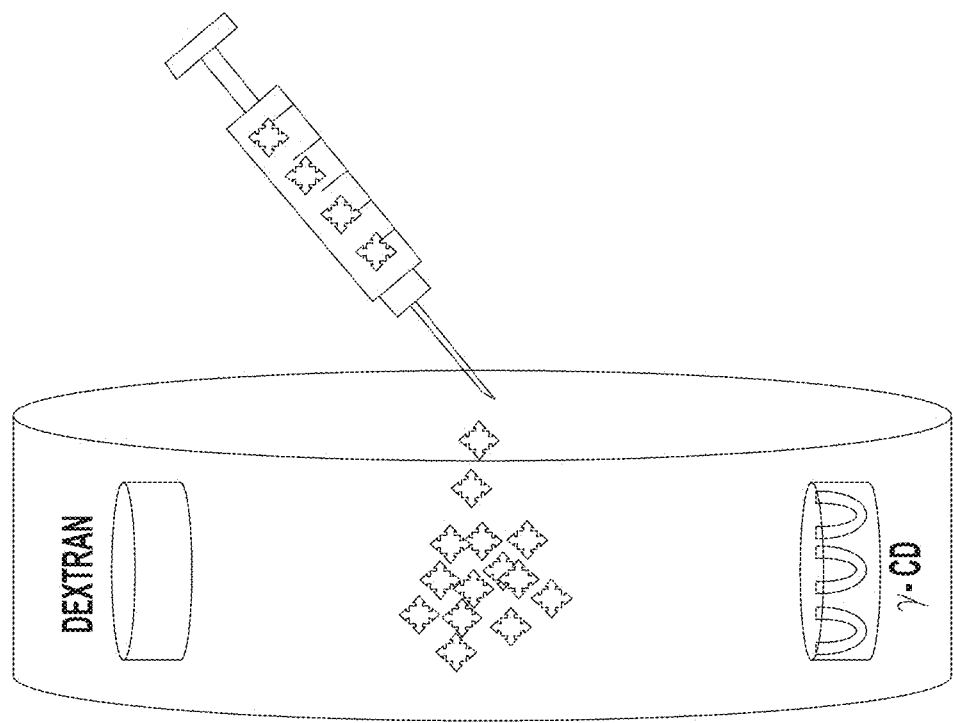
FIG. 13 provides an illustration showing an experimental setup for in vitro reloading of affinity-based polymer in a tissue. An empty dextran and γ-CD polymer were embedded in opposite ends of a tissue phantom, where DOX was injected in the center.

To assess whether the affinity-based polymer can be effectively reloaded, a competitive reloading assay was designed by embedding a γ-CD and a dextran polymer in opposite ends of a tissue phantom in a closed environment (one well of a 6-well tissue culture plate) and inject 100 ng of DOX in the center to allow the drug to freely diffuse (FIG. 13). The tissue phantom consisted of 0.5% agarose in order to simulation an in vivo environment. Top-down fluorescence imaging using the well-scan mode in a plate reader was performed on the tissue phantom at selected time points for 54 hr. The scanning was done from left to right and top to down.

The above method is sufficient for examining the dynamics of reloading in detail; however, the setup is complex and the scanning time was ~45 min per image. A modified setup was employed to allow a larger scale experiment to be conducted. Briefly, affinity-based or dextran polymers were first placed on the bottom of 24-well plates and then covered in 0.5% agarose. Similarly, top-down fluorescence imaging using the well-scan mode (11×11 equally spaced scanning points) was performed on the 24-well plate using Synergy H1 with an excitation and emission wavelength of 49 nm and 59 nm, respectively.

Image Registration for Processing Reloading Data

The goal of image registration was to efficiently analyze the reloading data by distinguishing the pixels that represented the polymer from those that represented the tissue phantom. First, raw fluorescence image data (11×11 pixels) were extracted using MATLAB. A grayscale display range was defined with a high and low value. The low value was displayed as pure white, indicating no DOX. The high value was displayed as pure black, which was based on the highest pixel intensity value found in these experiments. Next, the pixels representing the tissue phantom were distinguished from the pixels representing the polymer via 2D image registration algorithm developed using MATALB. First, a template image with predefined areas of both tissue phantom (lighter shades of grey) and polymer (darker shades of grey) was constructed. The polymer consisted of pixels of darker shades of grey than those of the tissue phantom; this was a representation of the well at the endpoint of a reloading experiment, assuming the polymer would exhibit higher intensity of signal due to loaded DOX. Then, an input image with unknown areas for both tissue phantom and polymer was registered against the template image. The input image was systematically shifted in both the x and y direction; with each iteration of shifting, 2D correlation between the two images was calculated. The registration algorithm then searched for scale parameters in both the x and y direction that would maximize 2D correlation between the two images, ultimately resulting in an overlaid image. The resulting scale parameters were then applied to the input image to determine the pixels representing the previously unknown areas of polymer in the tissue phantom.

In order for the algorithm to work properly, an assumption was made that the area of the polymer was the same among all samples. This is a valid assumption because all polymers were formed under a 10 mm diameter metal punch prior to use. The accuracy of the algorithm was confirmed by randomly selecting a sample and manually checking the registration results.

Quantification of Percent Reloading of DOX

Percent reloading of DOX into polymer is defined as (mass of DOX loaded into polymer/mass of injected DOX)× 100%. Mass of DOX loaded in the polymer, however, cannot be simply calculated based on calibration curve of the polymer loaded with different amounts of DOX. It is well known that DOX exhibits significant self-quenching at concentrations >10 µM. This phenomenon was verified experimentally with calibration curves and also reported in literature. Chaires et al., Biochemistry-Us 21, 3927 (1982). Hence, it was inconvenient to determine mass of DOX loaded in the polymer if the concentration exceeded 10 µM. Alternatively, because the concentration of DOX is much lower in the tissue phantom, a calibration curve was developed based on varying DOX concentrations in tissue phantoms. Mass of DOX loaded into the polymer can then be calculated by (mass of injected DOX—mass of DOX in the tissue phantom).

In Vivo Reloading of Affinity-Based Polymer

The polymer synthesis conditions (γ-CD (1:0.16)) that yielded the best percent reloading were used to fabricate the polymers used in the in vivo study. First, we implanted empty γ-CD (1:0.16) and dextran polymers (n=5) subcutaneously in the flanks of nude mice under gas anesthesia (2.5% isoflurane). At two time points that were one week apart, subcutaneous injections of 100 ng of DOX were performed near the polymer. To avoid skin lesions, the dose was limited to 100 ng. For 48 hr after each injection, reloading was monitored using fluorescence imaging with Xenogen IVIS equipped with a DsRed filter, of which the excitation and emission ranges overlap with that of DOX. The exposure time was 0.5 sec and the aperture was f8. Fluorescence signal from a drawn region of interest (ROI), was expressed in terms photon flux (photons/sec) and obtained using Living Image Software. All mice were placed on wheat-based diets to limit the effects of autofluorescence.

In Vitro Release of DOX from Affinity-Based Polymers

β-CD, γ-CD, and dextran polymers (n=3) were loaded in 4 ml of a 10 mg/ml DOX solution for 72 hr, at which point equilibrium was reached. Before transferring the loaded polymers for release, each sample was rinsed briefly with PBS to rid the potential DOX that had accumulated on the surface of the polymer. This was meant to minimize the possibility of an artificial 'burst release.' For in vitro release, the DOX-loaded polymers were placed in 2 ml of DMEM supplemented with 10% fetal bovine serum at 37° C. under gentle agitation. Instead of the commonly used PBS, we chose to use cell culture medium to better mimic the in vivo environment. DOX loading was characterized in an independent set of experiments involving extraction of similarly loaded polymers (n=3) using DMSO. The average of the total extracted amount was assumed to be the total amount of DOX loaded into respective polymers, and used for percent release calculations. At predetermined time points, two samples were aliquoted from each release medium: one for quantifying DOX release via fluorescence spectroscopy (ex: 498 nm; em: 590 nm) and the other for applying to a cancer cell line in vitro to test for bioactivity of the released DOX. The release medium was then replaced with fresh medium in order to maintain sink condition.

Cell Viability Assays

100 µl of human Lewis Lung Carcinoma cells (7500 cells/well) were cultured in 96-well plates in DMEM supplemented with 10% fetal bovine serum and 1% penicillin G sodium and streptomycin sulfate. After 24 hr, the medium was replaced by 100 µl of DOX-containing medium that was previously collected from the release medium of β-, γ-CD, and dextran polymers at selected time points (n=3). These previous samples were protected from light and stored at 4° C. until use. After another 24 hr incubation, 20 µl of a 5 mg/ml MTT solution was added to each well. The cells were incubated for 3 hr and the medium was then replaced by 200 µl of DMSO. After 30 min incubation, the plate was read using Synergy H1 with an absorbance wavelength of 590 nm. The results were normalized to readings from a set of wells with cells treated with no DOX, which represented 100% survival. Percent cell death was defined as 1-percent survival.

A similar procedure was used when testing the cytoxicity of DOX against U-87 MG, a human glioblastoma cell line. However, instead of previously collected DOX solution, DOX solutions at desired concentrations were made fresh for this assay.

Human Glioblastoma Xenograft Model in Mice

U-87 MG-luc2 cells, a luciferase expressing human glioblastoma cell line, were cultured in DMEM supplemented with 2 mM L-glutamine, 100 units/ml penicillin G sodium, 100 µg/ml streptomycin sulfate, 0.25 µg/ml amphotericin B, 1 mM sodium pyruvate and 10% fetal bovine serum prior to use in animal studies. Tumors were induced via subcutaneous injections of $0.5 \times 10^6$ U-87 MG-luc2 cells into the right flanks of 6-8 week old female athymic nude mice. All animal experiments were reviewed and approved by the Institutional Animal Care and Use Committee (protocol#2011-0171).

In Vivo Efficacy of Affinity-Based Polymers

Tumors diameter reached approximately 4-5 mm on day 28-day 32 post-inoculation, at which point DOX-laden (~5 mg/polymer) β-CD (n=6) and γ-CD polymers (n=7) were surgically implanted directly underneath the tumors. Empty γ-CD polymers (n=6) were implanted as controls. While under gas anesthesia (2.5% isoflurane), incisions of ~1 cm were made ~5 mm away from the tumor prior to implantation of polymers to ensure wound healing would not interfere with tumor growth. Wounds were closed using EZ clips.

Tumor growth was monitored via bioluminescence imaging with Xenogen IVIS. 20 minutes prior to imaging with Xenogen, mice received intraperitoneal injections of 200 µl of 15 mg/mL D-luciferin (100 µl on each side). D-luciferin potassium salt was dissolved in DPBS. For bioluminescence imaging, exposure time was set to be 0.5 min and the aperture set to be f8. The bioluminescence signal from a drawn region of interest (ROI), was expressed in terms photon flux (photons/sec) and obtained using Living Image Software. In addition to bioluminescence imaging, fluorescence imaging (described earlier) was performed on mice at each time point to monitor the DOX-loaded polymers.

Tumor volume was estimated based on digital caliper measurement. Tumor shape was assumed to be a hemiellipsoid; volume was calculated by:

$$V = \frac{\pi}{6} lwh$$

where l, w, and h, represent the length, width, and height of the tumor. Tumor weight was estimated based on tumor volume, assuming a density of 1 g/cm³. Mice were euthanized when tumor weight exceeded 10% of body weight.

Histology

Samples of tumor tissue were obtained prior to euthanizing mice. Tumor tissues are fixed in 10% formalin overnight and transferred to into PBS. After mechanized processing overnight, the tissues were then embedded in paraffin. 5 μm sections were sliced and then air dry. After melting off the paraffin, the slides were first stained with two xylenes to remove any remaining paraffin, and then rehydrated through graded ethanols to stain in hematoxylin. The slides are then taken through graded ethanols to eosin. Finally, slides were rinsed with five changes of 100% ethanol and two changes of xylene.

Efficacy of Reloadable Affinity-Based Polymer in Tumor-Bearing Mice

To test the therapeutic efficacy of in vivo reloading, a treatment model was developed in mice to mimic resection surgery followed by Gliadel® implantation in human GBM patients. In mice with size-matched tumors (~8 mm in diameter), a 6 mm biopsy punch was used to resect the central region of the tumor, creating a void where we then implanted empty γ-CD or dextran polymers (n=5). Mice were allowed to recover from surgery for 4 days. Then 100 ng of DOX was injected near γ-CD or dextran polymers. Vehicle injections of DPBS were also performed in another set of mice (n=5) implanted with empty γ-CD polymers. Tumor progression and the polymers were then monitored using similar methods described earlier.

Example 2: Effect of Cyclodextrin Amount on Affinity-Based Release

The mechanism controlling the rate of release in a typical polymer delivery system is primarily based on diffusion, with solubility also being a factor for some active agents. A number of researchers have added free cyclodextrin to polymer delivery systems to increase the solubility of a drug being delivered by the system. Accordingly, earlier efforts to use cyclodextrin in polymeric delivery systems resulted in faster delivery of the drug, compared with similar systems lacking the cyclodextrin. In these cases, the cyclodextrin would leave the polymer delivery system and continue to surround the drug with a cyclodextrin cage to improve solubility of the drug. The present invention, on the other hand, is generally directed to slowing down the rate of release of the drug, by keeping the drug within the delivery system, and holding it in place with the cyclodextrin (CD) pocket. The rate of release for drug from a delivery system in which cyclodextrin remains associated with the delivery system is dependent on both the rate that drug diffuses out of the device and the rate at which drug is able to escape from the CD pocket.

The inventors have also made the unexpected discovery that varying the amount of CD to dextran, which is a chemical similar to CD but is incapable of forming affinity complexes, had a significant effect on the rate of drug release from the drug delivery system. This appeared to be due to the fact that a lot of CD pockets had to be present for there to be a change in release rate that relies on drug affinity. In a blending study a blend of 75% CD still had about the same release rate as compositions having fewer pockets. However, at about 90% pockets, a markedly slower release rate was seen. In other compositions the exact ratio of CD to dextran required to show slower affinity-based release changed, depending on the chemistry, but for an affinity release profile to be seen, a large number of CD pockets had to be present.

Figure 14:
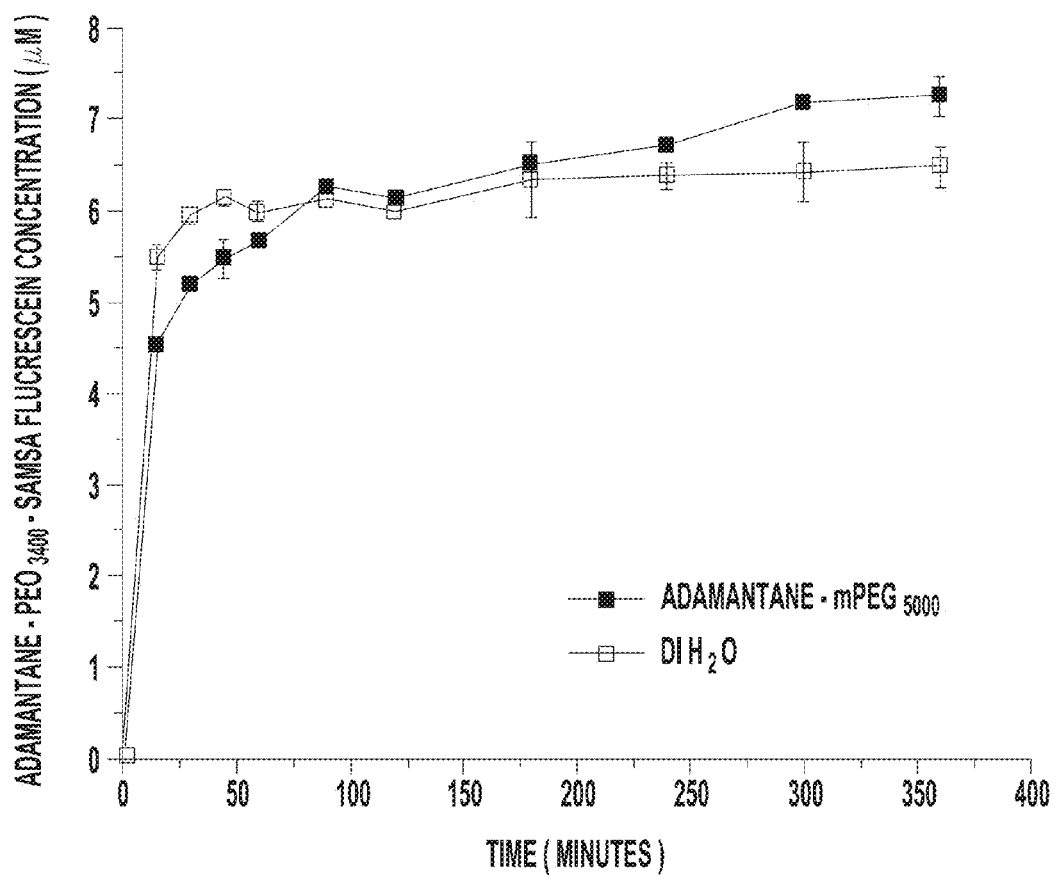
FIG. 14 provides a graph showing the release of adamantane-$PEG_{3400}$-SAMSA fluorescein from EVOH-β-cyclodextrin/$mPEG_{5000}$ films. The adamantane-$PEG_{3400}$-SAMSA fluorescein was previously bound to the film, and then substantially released. Water and non-fluorescent adamantine-$mPEG_{5000}$ were then administered to the film to see if the non-fluorescent admantine-$mPEG_{5000}$ was able to stimulate the release of any remaining adamantane-$PEG_{3400}$-SAMSA fluorescein, which in fact it did.
Figure 15:
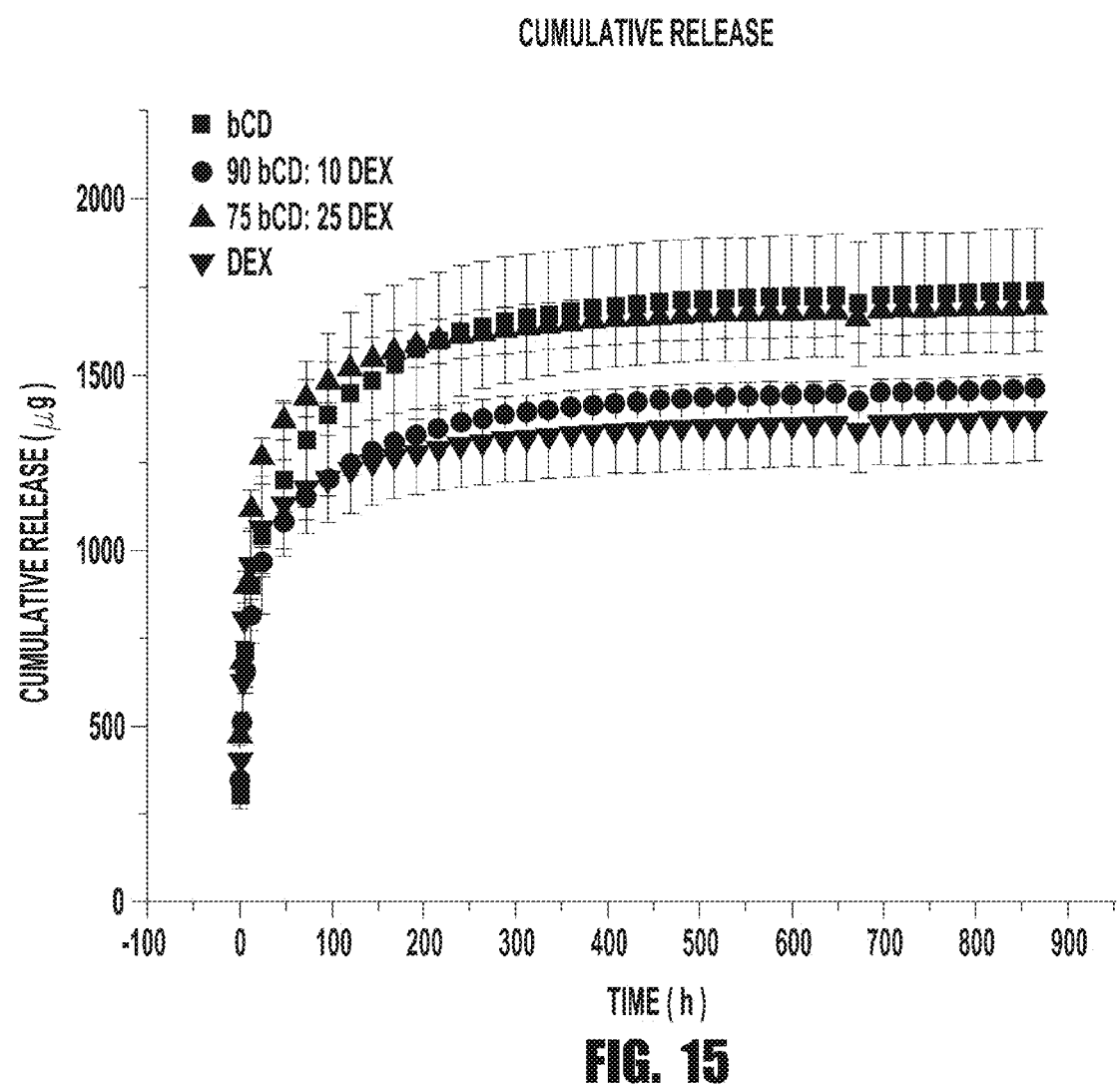
FIG. 15 provides a graph showing that at 90% CD and 10% dextran, the release rate is similar to that of pure CD, and shows an affinity-based release profile, while in this formulation 75% CD and 25% dextran is more similar to that of pure dextran and shows no affinity-based release. The Y axis of the graph corresponds to the cumulative mass of rifampicin release, while the X axis shows the time. All new polymers were made in 50/50 DMSO/DMF in which CD and dextran monomers were both soluble.
Figure 16:
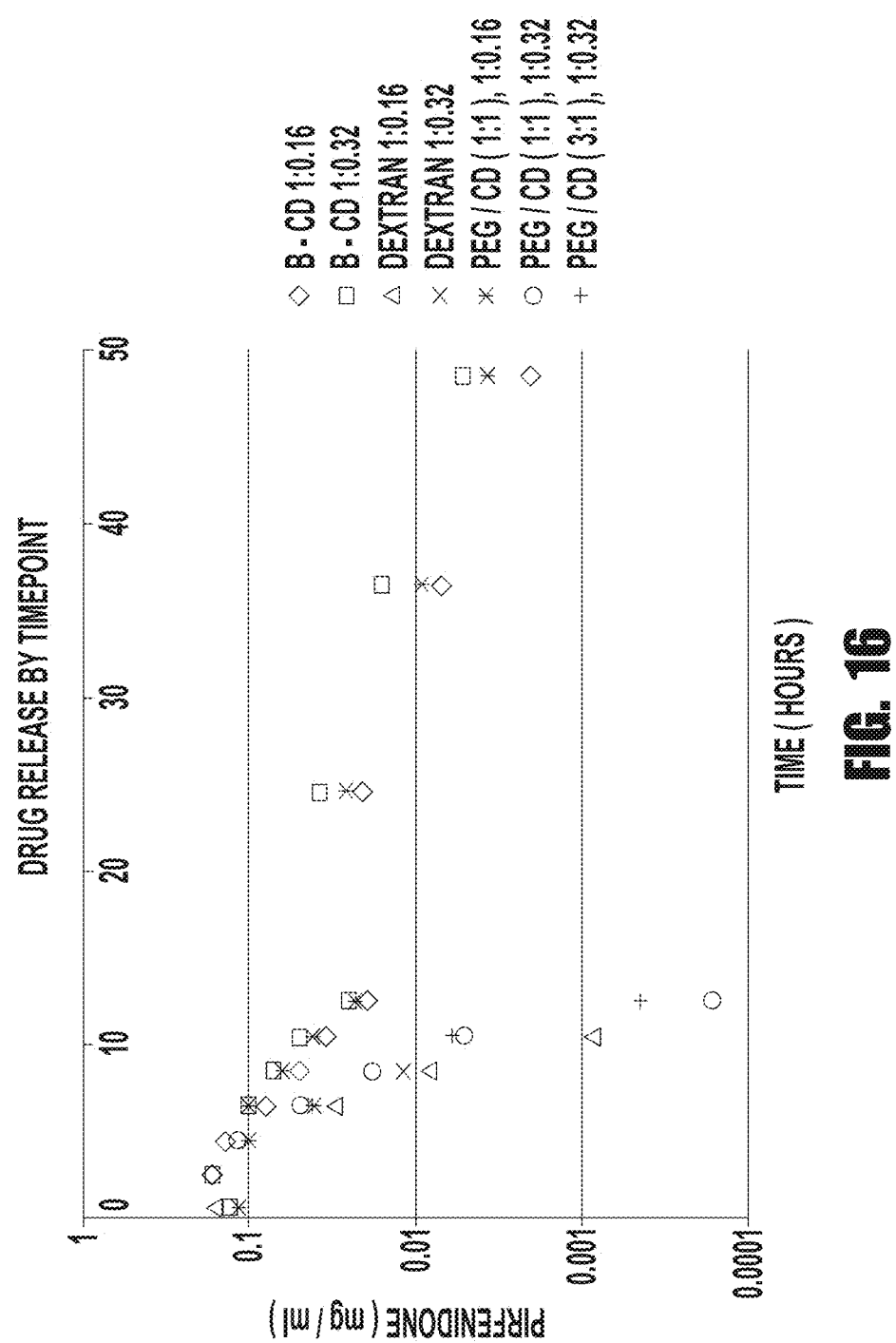
FIG. 16 provides a graph showing the release of perfenidone over time for polymers which are 100% β-CD, 100% dextran, or blends of CD and PEG at different ratios. In polymer blends where there was a 3:1 mass ratio of PEG to CD, release was very rapid, similar to non-affinity dextran only controls. In polymer blends where there was a 1:1 mass ratio of PEG to CD there were two different results based on the crosslinking ratio (and therefore the amount of CD incorporated). In high crosslink ratios, having more PEG, release was similar to non-affinity controls. In lower cross-linking ratios, having less PEG, release was similar to 100% CD affinity release controls.

The results of the experiments directed to showing the amount of CD necessary to provide affinity-based release are shown in FIGS. 14-16. As shown in FIG. 14, attaching CD as a pendant group to a polyvinyl alcohol backbone resulted in no detectable differences in release with substitution ratios up to 15% CD, which was the highest amount of CD that could be incorporated into this type of polymer. However, as shown in FIG. 15, at sufficiently high levels, incorporation of CD into a polymer will result in affinity-based release. In FIG. 15, the results of replacing CD with chemically similar dextran, which lacks the capacity to form affinity inclusions, can be seen. As 75% CD, the release rate from the polymer is similar to that of pure dextran; i.e., you see non-affinity based release. However, at 90% CD and 10% dextran, an affinity-based release profile is seen.

FIG. 16 shows the results of studies in which different ratios of CD and Dextran, a chemically similar material without the capacity to form high-affinity drug inclusions, were used. The results show that in this composition at 75% CD only regular diffusion release was shown. However at 90% CD the delivery profile changes to look more like the 100% CD sample. The unexpected finding illustrated by this figure is that a substantial change in release rate only occurs when the right amount of affinity moieties is reached.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for delivering a therapeutic guest agent to a subject, comprising:
   placing a therapeutic guest agent in an implantable or an injectable delivery platform at a desired location in the subject, the said delivery platform comprising a polymer substrate, at least one cyclodextrin host molecule coupled to the substrate, and therapeutic guest agent that is reversibly coupled to the host molecule;
   allowing the therapeutic guest agent to be released from the host molecule at the desired location; and
   reloading the therapeutic guest agent in the said delivery platform by contacting the said therapeutic agent delivery platform with additional injected therapeutic guest agent.

2. The method of claim 1, wherein the therapeutic guest agent has a degradation rate that is slower than the release rate of the therapeutic guest agent from the host molecule.

3. The method of claim 1, wherein the therapeutic agent comprises an anticancer agent.

4. The method of claim 3, wherein the therapeutic agent comprises doxorubicin.

5. The method of claim 1, wherein the cyclodextrin host molecule is selected from the group consisting of α-cyclodextrin, β-cyclodextrin, and γ-cyclodextrin.

6. The method of claim 1, wherein a plurality of cyclodextrin host molecules are present, and at least a portion of the cyclodextrin host molecules are crosslinked to other cyclodextrin host molecules.

7. The method of claim 1, wherein the release rate of the therapeutic guest agent is adjusted by complexing a tuning molecule to one or both of the therapeutic guest agent and the host molecule.

8. The method of claim 1, wherein a plurality of cyclodextrin host molecules define a plurality of pockets.

9. The method of claim 1, wherein the delivery platform provides a sustained release of the guest agent for at least 4 weeks.

10. The method of claim 1, wherein at least 50% by weight of cyclodextrin is coupled to the polymer substrate.

11. The method of claim 10, wherein at least 90% by weight of cyclodextrin is coupled to the polymer substrate.

12. A method of treating cancer in a subject in need thereof by placing an implantable or an injectable delivery platform at a desired location in the subject, the said delivery platform comprising a polymer substrate, at least one cyclodextrin host molecule coupled to the substrate, and an anticancer agent that is reversibly coupled to the host molecule;
 allowing the anticancer agent to be released from the host molecule at the desired location; and
 reloading the said delivery platform by contacting the said delivery platform with additional injected anticancer agent.

13. The method of claim 12, wherein the cancer is glioblastoma multiforme.

14. The method of claim 12, wherein the anticancer agent is doxorubicin.

15. The method of claim 12, wherein the desired location is a tumor site.

16. The method of claim 12, wherein the release rate of the anticancer agent is adjusted by complexing a tuning molecule to one or both of the anticancer agent and the host molecule.

17. The method of claim 12, wherein the therapeutic guest agent delivery platform provides a sustained release of the anticancer agent for at least 4 weeks.

* * * * *